(12) United States Patent
Huey et al.

(10) Patent No.: US 12,076,448 B2
(45) Date of Patent: *Sep. 3, 2024

(54) HEMOSTATIC DEVICES

(71) Applicant: Z-Medica, LLC, Wallingford, CT (US)

(72) Inventors: Raymond J. Huey, Orange, CT (US); Denny Lo, Bethlehem, CT (US); Daniel J. Burns, Stratford, CT (US); Giacomo Basadonna, Haddam, CT (US); Francis X. Hursey, West Hartford, CT (US)

(73) Assignee: TELEFLEX LIFE SCIENCES II LLC, Wilmington, DE (US)

( * ) Notice: Subject to any disclaimer, the term of this patent is extended or adjusted under 35 U.S.C. 154(b) by 108 days.

This patent is subject to a terminal disclaimer.

(21) Appl. No.: 17/407,026

(22) Filed: Aug. 19, 2021

(65) Prior Publication Data
US 2021/0379238 A1 Dec. 9, 2021

Related U.S. Application Data

(63) Continuation of application No. 17/178,047, filed on Feb. 17, 2021, now Pat. No. 11,123,451, which is a
(Continued)

(51) Int. Cl.
*A61L 15/44* (2006.01)
*A61F 13/00* (2006.01)
(Continued)

(52) U.S. Cl.
CPC ........ *A61L 15/44* (2013.01); *A61F 13/00012* (2013.01); *A61F 13/00063* (2013.01);
(Continued)

(58) Field of Classification Search
CPC ......... A61F 13/00012; A61F 13/00063; A61L 15/18; A61L 15/425; A61L 2400/04
See application file for complete search history.

(56) References Cited

U.S. PATENT DOCUMENTS

| 2,688,586 A | 9/1954 | Eberl et al. |
| 2,922,719 A | 1/1960 | Robinson |

(Continued)

FOREIGN PATENT DOCUMENTS

| CA | 1 223 208 | 6/1987 |
| CN | 101104080 | 1/2008 |

(Continued)

OTHER PUBLICATIONS

US 9,730,957 B2, 08/2017, Basadona et al. (withdrawn)
(Continued)

*Primary Examiner* — Savitha M Rao
(74) *Attorney, Agent, or Firm* — Knobbe, Martens, Olson & Bear, LLP

(57) ABSTRACT

A hemostatic device for promoting the clotting of blood includes a gauze substrate, a clay material disposed on the gauze substrate, and also a polyol such as glycerol or the like disposed on the gauze substrate to bind the clay material. When the device is used to treat a bleeding wound, at least a portion of the clay material comes into contact with blood emanating from the wound to cause the clotting. A bandage that can be applied to a bleeding wound to promote the clotting of blood includes a flexible substrate and a gauze substrate mounted thereon. The gauze substrate includes a clay material and a polyol. A hemostatic sponge also includes a gauze substrate and a dispersion of hemostatic material and a polyol on a first surface of the substrate.

22 Claims, 5 Drawing Sheets

Related U.S. Application Data continuation of application No. 15/841,843, filed on Dec. 14, 2017, now Pat. No. 10,960,101, which is a continuation of application No. 15/090,072, filed on Apr. 4, 2016, now Pat. No. 9,867,898, which is a continuation of application No. 14/185,873, filed on Feb. 20, 2014, now Pat. No. 9,333,117, which is a continuation of application No. 13/759,963, filed on Feb. 5, 2013, now Pat. No. 9,078,782, which is a continuation of application No. 13/682,085, filed on Nov. 20, 2012, now Pat. No. 8,846,076, which is a continuation of application No. 13/363,270, filed on Jan. 31, 2012, now Pat. No. 8,343,537, which is a continuation of application No. 12/581,782, filed on Oct. 19, 2009, now Pat. No. 8,114,433, which is a continuation of application No. 11/715,057, filed on Mar. 6, 2007, now Pat. No. 7,604,819, which is a continuation-in-part of application No. 11/590,427, filed on Oct. 30, 2006, now Pat. No. 7,968,114.

(60) Provisional application No. 60/810,447, filed on Jun. 1, 2006, provisional application No. 60/808,618, filed on May 26, 2006.

(51) Int. Cl.
- *A61L 15/18* (2006.01)
- *A61L 15/28* (2006.01)
- *A61L 15/42* (2006.01)

(52) U.S. Cl.
CPC .............. *A61L 15/18* (2013.01); *A61L 15/28* (2013.01); *A61L 15/425* (2013.01); *A61L 2300/404* (2013.01); *A61L 2300/406* (2013.01); *A61L 2400/04* (2013.01); *A61L 2400/16* (2013.01)

(56) References Cited

U.S. PATENT DOCUMENTS

| | | |
|---|---|---|
| 2,969,145 A | 1/1961 | Hannuer, Jr. |
| 3,122,140 A | 2/1964 | Crowe et al. |
| 3,181,231 A | 5/1965 | Breck |
| 3,189,227 A | 6/1965 | Hobbs et al. |
| 3,366,578 A | 1/1968 | Michalko |
| 3,386,802 A | 6/1968 | Michalko |
| 3,538,508 A | 11/1970 | Young |
| 3,550,593 A | 12/1970 | Kaufman |
| 3,608,070 A | 9/1971 | Nouvel |
| 3,658,984 A | 4/1972 | Kamp |
| 3,698,392 A | 10/1972 | Vogt et al. |
| 3,723,352 A | 3/1973 | Warner et al. |
| 3,763,900 A | 10/1973 | Solms-Baruth et al. |
| 3,979,335 A | 9/1976 | Golovko et al. |
| 4,373,519 A | 2/1983 | Errede et al. |
| 4,374,044 A | 2/1983 | Schaefer et al. |
| 4,379,143 A | 4/1983 | Sherry et al. |
| 4,435,512 A | 3/1984 | Ito et al. |
| 4,460,642 A | 7/1984 | Errede et al. |
| 4,514,510 A | 4/1985 | Alexander |
| 4,524,064 A | 6/1985 | Nambu |
| 4,525,410 A | 6/1985 | Hagiwara et al. |
| 4,569,343 A | 2/1986 | Kimura et al. |
| 4,626,550 A | 12/1986 | Hertzenberg |
| 4,631,845 A | 12/1986 | Samuel et al. |
| 4,651,725 A | 3/1987 | Kifune et al. |
| 4,717,735 A | 1/1988 | Stem |
| 4,728,323 A | 3/1988 | Matson |
| 4,748,978 A | 6/1988 | Kamp |
| 4,822,349 A | 4/1989 | Hursey et al. |
| 4,828,081 A | 5/1989 | Nordstrom et al. |
| 4,828,832 A | 5/1989 | DeCuellar et al. |
| 4,911,898 A | 3/1990 | Hagiwara et al. |
| 4,938,958 A | 7/1990 | Niira et al. |
| 4,956,350 A | 9/1990 | Mosbey |
| 5,140,949 A | 8/1992 | Chu et al. |
| 5,144,016 A | 9/1992 | Skjak-Braek et al. |
| 5,146,932 A | 9/1992 | McCabe |
| 5,271,943 A | 12/1993 | Bogart et al. |
| 5,474,545 A | 12/1995 | Chikazawa |
| 5,482,932 A | 1/1996 | Thompson |
| 5,486,195 A | 1/1996 | Myers et al. |
| 5,502,042 A | 3/1996 | Gruskin et al. |
| 5,538,500 A | 7/1996 | Peterson |
| 5,556,699 A | 9/1996 | Niira et al. |
| 5,575,995 A | 11/1996 | Giovanoni |
| 5,578,022 A | 11/1996 | Scherson et al. |
| 5,597,581 A | 1/1997 | Kaessmann et al. |
| 5,599,578 A | 2/1997 | Butland |
| D386,002 S | 11/1997 | Hinkle |
| 5,696,101 A | 12/1997 | Wu et al. |
| 5,716,337 A | 2/1998 | McCabe et al. |
| 5,725,551 A | 3/1998 | Myers et al. |
| 5,728,451 A | 3/1998 | Langley et al. |
| 5,766,715 A | 6/1998 | Garconnet |
| 5,788,682 A | 8/1998 | Maget |
| 5,801,116 A | 9/1998 | Cottrell et al. |
| 5,826,543 A | 10/1998 | Raymond et al. |
| 5,855,570 A | 1/1999 | Scherson et al. |
| 5,891,074 A | 4/1999 | Cerarczyk |
| 5,916,511 A | 6/1999 | Kotani et al. |
| 5,941,897 A | 8/1999 | Myers |
| 5,964,239 A | 10/1999 | Loux et al. |
| 5,964,349 A | 10/1999 | Odagiri |
| 5,981,052 A | 11/1999 | Siguyama |
| 5,993,964 A | 11/1999 | Nakajima |
| 6,037,280 A | 3/2000 | Edwards et al. |
| 6,060,461 A | 5/2000 | Drake |
| 6,086,970 A | 7/2000 | Ren |
| 6,123,925 A | 9/2000 | Barry et al. |
| 6,159,232 A | 12/2000 | Nowakowski |
| 6,187,347 B1 | 2/2001 | Patterson et al. |
| 6,203,512 B1 | 3/2001 | Farris et al. |
| 6,251,423 B1 | 6/2001 | Brandford |
| 6,372,333 B1 | 4/2002 | Sugiyama et al. |
| 6,428,800 B2 | 8/2002 | Greenspan et al. |
| 6,450,537 B2 | 9/2002 | Norris |
| 6,475,470 B1 | 11/2002 | Kayane et al. |
| 6,481,134 B1 | 11/2002 | Aledo |
| 6,486,285 B2 | 11/2002 | Fujita |
| 6,495,367 B1 | 12/2002 | Isogawa et al. |
| 6,523,778 B2 | 2/2003 | Key et al. |
| 6,573,419 B2 | 6/2003 | Naimer |
| 6,590,337 B1 | 7/2003 | Nishikawa et al. |
| 6,622,856 B2 | 9/2003 | Gallo et al. |
| 6,630,140 B1 | 10/2003 | Grunstein |
| 6,638,073 B1 | 10/2003 | Kazimirov et al. |
| 6,685,227 B2 | 2/2004 | Merry et al. |
| 6,700,032 B1 | 3/2004 | Gray |
| 6,701,649 B1 | 3/2004 | Brosi |
| 6,745,720 B2 | 6/2004 | Rasner et al. |
| 6,805,961 B1 | 10/2004 | Watanabe et al. |
| 6,890,177 B2 | 5/2005 | Dragan |
| 6,998,510 B2 | 2/2006 | Buckman et al. |
| 7,125,821 B2 | 10/2006 | Xu et al. |
| 7,303,759 B2 | 12/2007 | Mershon |
| 7,322,976 B2 | 1/2008 | Yassinzadeh |
| 7,371,403 B2 | 5/2008 | McCarthy et al. |
| 7,429,252 B2 | 9/2008 | Sarangapani |
| 7,572,274 B2 | 8/2009 | Yassinzadeh |
| 7,595,429 B2 | 9/2009 | Hursey |
| 7,604,819 B2 | 10/2009 | Huey et al. |
| 7,691,127 B2 | 4/2010 | Yassinzadeh |
| 7,815,640 B2 | 10/2010 | Yassinzadeh |
| 7,825,133 B2 | 11/2010 | Yi |
| 7,858,123 B2 | 12/2010 | Stucky |
| 7,968,114 B2 | 6/2011 | Huey et al. |
| 7,993,366 B2 | 8/2011 | Yassinzadeh et al. |
| 8,063,264 B2 | 11/2011 | Spearman et al. |
| 8,114,433 B2 | 2/2012 | Huey et al. |
| 8,118,777 B2 | 2/2012 | Ducharme et al. |
| 8,202,532 B2 | 6/2012 | Huey et al. |

(56) References Cited

U.S. PATENT DOCUMENTS

| | | |
|---|---|---|
| 8,252,318 B2 | 8/2012 | Huey et al. |
| 8,252,344 B2 | 8/2012 | Hursey |
| 8,257,731 B2 | 9/2012 | Horn et al. |
| 8,257,732 B2 | 9/2012 | Huey et al. |
| 8,277,837 B2 | 10/2012 | Fischer et al. |
| 8,323,305 B2 | 12/2012 | Epstein et al. |
| 8,343,537 B2 | 1/2013 | Huey et al. |
| 8,361,054 B2 | 1/2013 | Ducharme et al. |
| 8,383,148 B2 | 2/2013 | Huey et al. |
| 8,439,944 B2 | 5/2013 | Yassinzadeh |
| 8,444,671 B2 | 5/2013 | Yassinzadeh |
| 8,460,699 B2 | 6/2013 | Huey et al. |
| 8,497,408 B2 | 7/2013 | Whek et al. |
| 8,512,743 B2 | 8/2013 | Horn et al. |
| 8,535,709 B2 | 9/2013 | Kennedy et al. |
| 8,557,278 B2 | 10/2013 | Huey et al. |
| 8,703,634 B2 | 4/2014 | Baker et al. |
| 8,747,435 B2 | 6/2014 | Yassinzadeh |
| 8,784,876 B2 | 7/2014 | Huey et al. |
| 8,846,076 B2 | 9/2014 | Huey et al. |
| 8,858,969 B2 | 10/2014 | Pahari et al. |
| 8,911,472 B2 | 12/2014 | Yassinzadeh et al. |
| 8,938,898 B2 | 1/2015 | Lo et al. |
| 9,017,374 B2 | 4/2015 | Yassinzadeh |
| 9,072,806 B2 | 7/2015 | Lo et al. |
| 9,078,782 B2 | 7/2015 | Huey et al. |
| 9,179,897 B2 | 11/2015 | Yassinzadeh et al. |
| 9,333,117 B2 | 5/2016 | Huey et al. |
| 9,352,066 B2 | 5/2016 | Dubey |
| 9,370,347 B2 | 6/2016 | Yassinzadeh |
| 9,427,221 B2 | 8/2016 | Yassinzadeh |
| 9,439,637 B2 | 9/2016 | Yassinzadeh et al. |
| 9,597,066 B2 | 3/2017 | Yassinzadeh et al. |
| 9,603,964 B2 | 3/2017 | Dubey et al. |
| 9,839,772 B2 | 12/2017 | Ducharme |
| 9,867,898 B2 | 1/2018 | Huey et al. |
| 9,867,931 B2 | 1/2018 | Gittard |
| 9,889,154 B2 | 2/2018 | Basadonna et al. |
| 10,086,106 B2 | 10/2018 | Huey et al. |
| 10,130,347 B2 | 11/2018 | Yassinzadeh |
| 10,960,100 B2 | 3/2021 | Dubey et al. |
| 10,960,101 B2 | 3/2021 | Huey et al. |
| 11,007,218 B2 | 5/2021 | Basadonna et al. |
| 11,123,451 B2 | 9/2021 | Huey et al. |
| 11,559,601 B2 | 1/2023 | Dubey et al. |
| 2002/0077653 A1 | 6/2002 | Hudson et al. |
| 2002/0141964 A1 | 10/2002 | Patterson et al. |
| 2002/0197302 A1 | 12/2002 | Cochrum et al. |
| 2003/0018357 A1 | 1/2003 | Luthra et al. |
| 2003/0133990 A1 | 7/2003 | Hursey et al. |
| 2003/0165560 A1 | 9/2003 | Otsuka et al. |
| 2003/0175333 A1 | 9/2003 | Shefer et al. |
| 2003/0176828 A1 | 9/2003 | Buckman et al. |
| 2003/0181917 A1 | 9/2003 | Gertner |
| 2003/0199922 A1 | 10/2003 | Buckman |
| 2003/0208150 A1 | 11/2003 | Bruder et al. |
| 2003/0212357 A1 | 11/2003 | Pace |
| 2004/0005350 A1 | 1/2004 | Looney et al. |
| 2004/0013715 A1 | 1/2004 | Wnek et al. |
| 2004/0038893 A1 | 2/2004 | Ladner et al. |
| 2004/0121027 A1 | 6/2004 | Pushpangadan et al. |
| 2004/0121438 A1 | 6/2004 | Quirk |
| 2004/0131820 A1 | 7/2004 | Turner et al. |
| 2004/0166172 A1 | 8/2004 | Rosati et al. |
| 2004/0166758 A1 | 8/2004 | Reichmann et al. |
| 2004/0169033 A1 | 9/2004 | Kuibira et al. |
| 2004/0243043 A1 | 12/2004 | McCarthy et al. |
| 2005/0023956 A1 | 2/2005 | Kwak et al. |
| 2005/0058721 A1 | 3/2005 | Hursey |
| 2005/0070693 A1 | 3/2005 | Hansen et al. |
| 2005/0107826 A1 | 5/2005 | Zhu et al. |
| 2005/0118230 A1 | 6/2005 | Hill et al. |
| 2005/0119112 A1 | 6/2005 | Pfenninger et al. |
| 2005/0137512 A1 | 6/2005 | Campbell et al. |
| 2005/0143689 A1 | 6/2005 | Ramsey, III |
| 2005/0147656 A1 | 7/2005 | McCarthy et al. |
| 2005/0226911 A1 | 10/2005 | Bringley et al. |
| 2005/0246009 A1 | 11/2005 | Toner et al. |
| 2005/0248270 A1 | 11/2005 | Ghosh et al. |
| 2005/0249899 A1 | 11/2005 | Bonutti |
| 2005/0287239 A1 | 12/2005 | Joo et al. |
| 2006/0034935 A1 | 2/2006 | Pronovost et al. |
| 2006/0078628 A1 | 4/2006 | Koman et al. |
| 2006/0116635 A1 | 6/2006 | Heughten |
| 2006/0121101 A1 | 6/2006 | Ladizinsky |
| 2006/0127437 A1 | 6/2006 | Kennedy et al. |
| 2006/0141018 A1 | 6/2006 | Cochrum et al. |
| 2006/0141060 A1 | 6/2006 | Hursey et al. |
| 2006/0159733 A1 | 7/2006 | Pendharkar et al. |
| 2006/0172000 A1 | 8/2006 | Cullen et al. |
| 2006/0178609 A1 | 8/2006 | Horn et al. |
| 2006/0193905 A1 | 8/2006 | Ehringer et al. |
| 2006/0211965 A1 | 9/2006 | Horn et al. |
| 2006/0211971 A1 | 9/2006 | Horn et al. |
| 2006/0271094 A1 | 11/2006 | Hudson et al. |
| 2006/0282046 A1 | 12/2006 | Horn et al. |
| 2007/0004995 A1 | 1/2007 | Horn et al. |
| 2007/0016152 A1 | 1/2007 | Karpowicz et al. |
| 2007/0031515 A1 | 2/2007 | Stucky et al. |
| 2007/0065491 A1 | 3/2007 | Huey et al. |
| 2007/0104768 A1 | 5/2007 | Huey et al. |
| 2007/0104792 A1 | 5/2007 | Jenkins |
| 2007/0134293 A1 | 6/2007 | Huey et al. |
| 2007/0142783 A1 | 6/2007 | Huey et al. |
| 2007/0154509 A1 | 7/2007 | Wilcher et al. |
| 2007/0154510 A1 | 7/2007 | Wilcher et al. |
| 2007/0154564 A1 | 7/2007 | Stucky et al. |
| 2007/0160638 A1 | 7/2007 | Mentkow et al. |
| 2007/0160653 A1 | 7/2007 | Fischer et al. |
| 2007/0167971 A1 | 7/2007 | Huey et al. |
| 2007/0264315 A1 | 11/2007 | Fournie et al. |
| 2007/0275073 A1 | 11/2007 | Huey et al. |
| 2007/0276308 A1 | 11/2007 | Huey et al. |
| 2007/0276345 A1 | 11/2007 | Huey et al. |
| 2007/0281011 A1 | 12/2007 | Jenkins et al. |
| 2008/0027365 A1 | 1/2008 | Huey |
| 2008/0085300 A1 | 4/2008 | Huey et al. |
| 2008/0097271 A1 | 4/2008 | Lo et al. |
| 2008/0125686 A1 | 5/2008 | Lo |
| 2008/0131855 A1 | 6/2008 | Eggert et al. |
| 2008/0145455 A1 | 6/2008 | Bedard |
| 2008/0146984 A1 | 6/2008 | Campbell et al. |
| 2008/0154303 A1 | 6/2008 | Yassinzadeh |
| 2008/0199539 A1 | 8/2008 | Baker et al. |
| 2008/0206134 A1 | 8/2008 | Lo et al. |
| 2008/0254146 A1 | 10/2008 | Huey et al. |
| 2008/0254147 A1 | 10/2008 | Huey et al. |
| 2008/0269658 A1 | 10/2008 | Vinton et al. |
| 2008/0299226 A1 | 12/2008 | Mentkow et al. |
| 2008/0317831 A1 | 12/2008 | Lo |
| 2008/0319476 A1 | 12/2008 | Ward et al. |
| 2009/0008261 A1 | 1/2009 | Kotzeva et al. |
| 2009/0011394 A1 | 1/2009 | Meglan et al. |
| 2009/0018479 A1 | 1/2009 | McCarthy et al. |
| 2009/0043268 A1 | 2/2009 | Eddy et al. |
| 2009/0047366 A1 | 2/2009 | Bedard et al. |
| 2009/0053288 A1 | 2/2009 | Eskridge, Jr. et al. |
| 2009/0074880 A1 | 3/2009 | Ladizinsky |
| 2009/0076475 A1 | 3/2009 | Ross et al. |
| 2009/0112170 A1 | 4/2009 | Wells et al. |
| 2009/0123525 A1 | 5/2009 | Bedard |
| 2009/0155342 A1 | 6/2009 | Diegelmann et al. |
| 2009/0162406 A1 | 6/2009 | Basadonna et al. |
| 2009/0186013 A1 | 7/2009 | Stucky |
| 2009/0186071 A1 | 7/2009 | Huey et al. |
| 2009/0232902 A1 | 9/2009 | Liu et al. |
| 2009/0274769 A1 | 11/2009 | Fregonese |
| 2009/0299253 A1 | 12/2009 | Hursey |
| 2010/0035045 A1 | 2/2010 | McAmish |
| 2010/0047352 A1 | 2/2010 | Pronovost et al. |
| 2010/0079395 A1 | 4/2010 | Kim et al. |
| 2010/0121244 A1 | 5/2010 | Horn et al. |
| 2010/0158989 A1 | 6/2010 | Mentkow et al. |
| 2010/0168767 A1 | 7/2010 | Yassinzadeh |

(56) References Cited

U.S. PATENT DOCUMENTS

| | | |
|---|---|---|
| 2010/0172958 A1 | 7/2010 | Lucchesi et al. |
| 2010/0184348 A1 | 7/2010 | McAmish |
| 2010/0209531 A2 | 8/2010 | Stucky et al. |
| 2010/0228174 A1 | 9/2010 | Huey |
| 2010/0233248 A1 | 9/2010 | Huey et al. |
| 2010/0292624 A1 | 11/2010 | Diegelmann et al. |
| 2010/0324464 A1 | 12/2010 | Kamakura et al. |
| 2011/0015565 A1 | 1/2011 | Hursey |
| 2011/0059287 A1 | 3/2011 | McAmish |
| 2011/0064785 A1 | 3/2011 | Daniels |
| 2011/0150973 A1 | 6/2011 | Bowlin et al. |
| 2011/0229849 A1 | 9/2011 | Maurer et al. |
| 2011/0237994 A1 | 9/2011 | Russ et al. |
| 2011/0268784 A1 | 11/2011 | Huey |
| 2012/0004636 A1 | 1/2012 | Lo |
| 2012/0045742 A1 | 2/2012 | Meglan et al. |
| 2012/0070470 A1 | 3/2012 | Pahari |
| 2012/0130296 A1 | 5/2012 | Huey |
| 2012/0259262 A1 | 10/2012 | Huey |
| 2013/0041332 A1 | 2/2013 | Huey |
| 2013/0060279 A1 | 3/2013 | Yassinzadeh |
| 2013/0079695 A1 | 3/2013 | Huey |
| 2013/0178778 A1 | 7/2013 | Huey |
| 2013/0267923 A1 | 10/2013 | Huey |
| 2013/0344131 A1 | 12/2013 | Lo |
| 2014/0377362 A1 | 12/2014 | Pahari |
| 2015/0141301 A1 | 5/2015 | Rovison, Jr. et al. |
| 2015/0209019 A1 | 7/2015 | Yassinzadeh |
| 2015/0221238 A1 | 8/2015 | Huebner |
| 2016/0120901 A1 | 5/2016 | Basadonna |
| 2016/0141018 A1 | 5/2016 | Lin et al. |
| 2016/0213808 A1 | 7/2016 | Huey |
| 2016/0256142 A1 | 9/2016 | Yassinzadeh |
| 2016/0345946 A1 | 12/2016 | Yassinzadeh et al. |
| 2017/0151365 A1 | 6/2017 | Dubey et al. |
| 2017/0202546 A1 | 7/2017 | Yassinzadeh et al. |
| 2017/0296579 A1 | 10/2017 | Basadonna |
| 2018/0104378 A1 | 4/2018 | Huey et al. |
| 2018/0221006 A1 | 8/2018 | Yassinzadeh |
| 2018/0228934 A1 | 8/2018 | Huey |
| 2018/0271898 A1 | 9/2018 | Basadonna et al. |
| 2019/0167241 A1 | 6/2019 | Yassinzadeh et al. |
| 2021/0178013 A1 | 6/2021 | Huey et al. |
| 2023/0149592 A1 | 5/2023 | Dubey |
| 2024/0033398 A1 | 2/2024 | Huey |

FOREIGN PATENT DOCUMENTS

| | | |
|---|---|---|
| CN | 102209505 A | 1/2011 |
| CN | 102137684 A | 7/2011 |
| CN | 102164619 A | 8/2011 |
| CN | 201920992 U | 8/2011 |
| CN | 102274541 A | 12/2011 |
| CN | 101687056 | 8/2016 |
| EP | 0 107 051 | 9/1983 |
| EP | 0 296 324 | 12/1988 |
| EP | 0 353 710 | 2/1990 |
| EP | 0 826 822 | 3/1998 |
| EP | 0 888 783 | 7/1999 |
| EP | 1 159 972 | 5/2001 |
| EP | 1 714 642 | 10/2006 |
| EP | 2 446 867 | 5/2012 |
| GB | 548046 | 9/1942 |
| GB | 2 175 889 | 12/1986 |
| GB | 2 259 858 | 3/1993 |
| GB | 2 314 842 | 1/1998 |
| JP | S59-62050 | 9/1984 |
| JP | 61145120 | 7/1986 |
| JP | 01-096558 | 10/1987 |
| JP | 2-45040 | 2/1990 |
| JP | 9-504719 | 5/1997 |
| JP | 2777279 B2 | 7/1998 |
| JP | 10-337302 | 12/1998 |
| JP | 11-071228 | 3/1999 |
| JP | 11-178912 | 7/1999 |
| JP | 11-332909 A1 | 7/1999 |
| JP | 2002-530157 | 9/2002 |
| JP | 2002-331024 | 11/2002 |
| JP | 2003-66045 | 3/2003 |
| JP | 2003-305079 | 10/2003 |
| JP | 2005-015537 | 1/2005 |
| JP | 2004-123651 | 7/2006 |
| WO | WO 92/19802 | 11/1992 |
| WO | WO 95/05445 | 2/1995 |
| WO | WO 95/12371 | 5/1995 |
| WO | WO 96/40285 | 12/1996 |
| WO | WO 99/13918 | 3/1999 |
| WO | WO 00/30694 | 6/2000 |
| WO | WO 00/66086 | 11/2000 |
| WO | WO 01/082896 | 8/2001 |
| WO | WO 01/097826 | 12/2001 |
| WO | WO 02/030479 | 4/2002 |
| WO | WO 02/060367 | 8/2002 |
| WO | WO 02/074325 | 9/2002 |
| WO | WO 03/057072 | 7/2003 |
| WO | WO 03/074566 | 9/2003 |
| WO | WO 05/012493 | 2/2005 |
| WO | WO 05/030279 | 4/2005 |
| WO | WO 05/087280 | 9/2005 |
| WO | WO 05/123170 | 12/2005 |
| WO | WO 06/006140 | 1/2006 |
| WO | WO 06/012218 | 2/2006 |
| WO | WO 06/088912 | 8/2006 |
| WO | WO 06/102008 | 9/2006 |
| WO | WO 06/110393 | 10/2006 |
| WO | WO 07/120342 | 10/2007 |
| WO | WO 08/036225 | 3/2008 |
| WO | WO 08/054566 | 5/2008 |
| WO | WO 08/109160 | 9/2008 |
| WO | WO 08/127497 | 10/2008 |
| WO | WO 09/109194 | 9/2009 |
| WO | WO 14/047436 | 3/2014 |

OTHER PUBLICATIONS

"Mastering the Art of Innovative Thinking," (color brochure) FMC BioPolymer, 2001 FMC Corporation.
Acheson, et al.: "Comparison of Hemorrage Control Agents Applied to Lethal Extremity Arterial Hemorrages in Swine," The Journal of Trauma, Injury, Infection, and Critical Care, 2005:59 865-875.
Alam, et al., Application of a Zeolite Hemostatic Agent Achieves 100% Survival in a Lethal Model of Complex Groin Injury in Swine, May 2004, The Journal of Trauma Injury, Infection, and Critical Care, vol. 56, pp. 974-983.
Alam, et al., Comparative Analysis of Hemostatic Agents in a Swine Model of Lethal Groin Injury, Jun. 2003, The Journal of Trauma Injury, Infection, and Critical Care, vol. 54, No. 6, pp. 1077-1082.
Aldrich—Handbook of Fine Chemicals and Laboratory Equipment, 2000-2001, pp. 1177-1178.
Analgesics and Anti-inflammatory agents 2004, retrieved from the internet on May 26, 2010, URL: http://web.archive.org/web/20040904151322/http://faculty.weber.edu/ewalker/Medicinal_Chemistry/topics/Analgesia_antiinflam/Analgesics_anti-inflammatory.htm.
Angeloni, V., M.D.: "How to care for your wound.", Heartland Dermatology & Skin Cancer P. C., copyright 2001, V. Angeloni MD.
Army halts use of new first aid item to study more, Seattle PI, Dec. 24, 2008.
Army halts use of WoundStat, http://stripes.com, Apr. 23, 2009.
Army pulls anti-clotting agent after Fort Sam study finds threat, MySanAntonio Military, Dec. 24, 2008.
Baker, Sarah E. et al., Controlling Bioprocesses with Inorganic Surfaces: Layered Clay Hemostatic Agents, Department of Chemistry and Biochemistry, University of California, Santa Barbara, American Chemical Association 2007, 19, pp. 4390-4392 (3 pages total).
Basadonna, G., et al.: "A novel kaolin coated surgical gauze improves hemostasis both in vitro and in vivo", Journal of Surgical Research, vol. 144, No. 2, Feb. 2008, p. 440, XP002534658, abstract.

(56) References Cited

OTHER PUBLICATIONS

Bethesda, MD, TraumaCure, Life-saving News for Battlefield Soldiers & Wounded Civilians FDA Clears Product to Stop Severe Bleeding, Sep. 10, 2007.
Butenas—Mechanism of factor VIIa-dependent coagulation in hemophilia blood, Hemostasis, Thrombosis, and Vascular Biology, Blood, Feb. 1, 2002—vol. 99, No. 3.
Calcium Alginate, definition—Prepared at the 49th JECFA (1997), published in FNP 52 Add 5 (1997) superseding specifications prepared at the 44th JECFA (1995), published in FNP52, Add 3 (1995). An ADI 'not specified' was established at the 39th JECFA (1992).
Caloplast (Kaolin Poultrice), South African Electronic Package Inserts, Information presented by Malahide Information Systems, Copyright 1996-1998, printed from home.intekom.com/pharm/allied/caloplst.html#INDICATIONS, two pages.
Carraway, et al., Comparison of a new mineral based hemostatic agent to a commercially available granular zeolite agent for hemostasis in a swine model of lethal extremity arterial hemorrhage, Resuscitation vol. 78, Issue 2.
Clay makers (raw materials) retrieved from the internet on Mar. 15, 2010, URL: http://web.archive.org/web/20020609175053/http://www.claymaker.com/ceramic_central/info/raw_clays.htm (year 2002, pp. 104).
Comparative Testing of Hemostatic Dressings in a Severe Groin Hemorrhage, Trauma & Resuscitative Medicine Department, NMRC, Aug. 2008 (Part 2 of 3, pp. 10-19).
Comparative Testing of Hemostatic Dressings in a Severe Groin Hemorrhage, Trauma & Resuscitative Medicine Department, NMRC, Aug. 2008 (Part 3 of 3, pp. 20-29).
Comparative Testing of Hemostatic Dressings in a Severe Groin Hemorrhage, Trauma &Resuscitative Medicine Department, NMRC, Aug. 2008 (Part 1 of 3, pp. 1-9).
Connor, William E.: "The Acceleration of Thrombus Formatin by Certain Fatty Acids," Journal of Clinical Investigation, vol. 41, No. 6, 1962.
Curasorb Calcium Alginate Dressings information page, http://www.kendallhq.com/kendallhealthcare/pageBuilder.aspx?webPageID=0&topicID=70966&xsl=xsl/productPagePrint.xsl (last accessed May 22, 2012).
Davis et al., 1H—NMR Study of Na Alginates Extracted from *Sargassum* spp. in Relation to Metal Biosorption, 110 Applied Biochemistry and Biotechnology 75 (2003).
Dictionary of Traditional Chinese Medicine, "Astringents and Haemostatices," The Commercial Press, Ltd., Apr. 1984 [ISBN 962 07 3051 8], pp. 216-217, total 4 pages.
Dubick et al.: "New Technologies for Treating Severe Bleeding in Far-Forward Combat Areas," RTO-MP-HFM-182, 21-1 to 21-12. NATO/OTAN, US Army Institute of Surgical Research.
Dyer, A. et al. "Diffusion in heteroionic zeolites: part 1. Diffusion of water in heteroionics natrolites." Microporous and Mesoporous Materials. 1998. pp. 27-38. vol. 21.
Fruijtier-Polloth, "The safety of synthetic zeolites used in detergents", Arch Toxicol (2009) 83:23-25.
Gakkaishi, Sen'i: "General Information on Alginates and its Applications," Fibers and Industry, vol. 65, No. 12, pp. 444-448, 2009. (Publication showing well-known technology).
Galan, et al.: "Technical properties of compound kaolin sample from griva (Macedonia, Greece)", Applied Clay Science 1996 10:477-490.
Gibbar-Clements, et al.: "The Challenge of Warfarin Therapy", JSTOR: The American Journal of Nursing, vol. 100, No. 3 (Mar. 2000), pp. 38-40.
Gielen, M., Solid State Organometallic Chemistry: Methods and Applications Physical Organometallic Chemistry, 1999, New York John Wiley & Sons, Ltd. (UK), V. 2, p. 156.
Griffin, J. H.: "Role of surface in surface-dependent activation of Hageman factor (blood coagulation Factor XII)", Proc. Natl. Acad. Sci, USA, vol. 75, No. 4, pp. 1998-2002, Apr. 1978 Medical Sciences.

Hahn, Lynn: "High temperature 1H NMR to determine the relative amounts of guluronate and mannuronate in the sodium alginate sample", Intertek, ASA, Analytical Report, Report No. 60665 v 1, dated May 6, 2012.
Handbook of textile fibre structure, First Published 2009, p. 276, Par. 1. (1 page).
HemCon Medical Technologies Inc. 501 (k) Summary, ChitoGauze, Mar. 20, 2009.
Hempen, et al., A Materia Medica for Chinese Medicine, Plants minerals and animal products, Churchill Livingston Elsevier, 2009, [ISBN 978 0 443 10094 9], pp. 832-833 (Halloysitum rubrum, Chi shi zi), total 5 pages.
Hollister Wound Care Restore Calcium Alginate Dressing, Silver instruction manual and information booklet, available at http://hollisterwoundcare.com/files/pdfs/ifus/Restore907814B407ColorBreak.pdf (last accessed May 22, 2012).
Hsu, et al.: Oriental Materia Medica a concise guide. 1986 by the Oriental Healing Arts Institute.
Huang: The Pharmacology of Chinese Herbs, Second Edition. 1999 by CRC Press LLC.
Hubbard, et al.: "Ionic charges of glass surfaces and other materials, and their possible role in the coagulation of blood," Journal of Applied Physiology, Mar. 1, 1960, vol. 15, No. 2, pp. 265-270.
Hursey, et al., Bandage Using Molecular Sieves, Apr. 18, 2002, International Application Published Under the PCT, WO 02/30479 A1.
IMA-EU, Kaolin, Oct. 2006, p. 1-2.
Indian Office Action, re IN Application No. 11041/DELNP/2014, dated Nov. 5, 2020.
James, "Silver Copper Zeolite Guinea Pig Sensitization Study—Buehler Method", Data Evaluation Report dated Oct. 3, 1989.
Japanese Office Action re Application No. JP 2009-534569, dated Nov. 15, 2010.
Kamala,et al.: "Extraction and Characterization of Water Soluble Chitosan from Parapeneopsis Stylifera Shrimp Shell Waste and Its Antibacterial Activity," International Journal of Scientific and Research Publications, vol. 3, Issue 4, Apr. 2013.
Kheirabadi, Army Assessment of New Hemostatic Products Suitable for Treating Combat Wounds, US Army Institute of Surgical Research, Aug. 11, 2008.
Kheirabadi, et al., Session IV-B, Paper 28, 8:20 a.m., Comparison of New Hemostatic Dressings with Currently Deployed Hemcon Bandage in a Model of Extremity Arterial Hemorrhage in Swine.
Kheirabadi, et al., The Journal of Trauma Injury, Infection, and Critical Care, Comparison of New Hemostatic Granules/Powders with Currently Deployed Hemostatic Products in a Lethal model of Extremity Arterial Hemorrhage in Swine, Feb. 2009, pp. 316-328.
Kheirabadi, Final Report, Title: Assessment of Efficacy of New Hemostatic Agents in a Model of Extremity Arterial Hemorrhage in Swine, U.S. Army Institute of Surgical Research, Ft. Sam Houston, TX 78234, Mar. 4, 2008.
Kovzun, I. G., et al.: "Application of nanosize clay-mineral systems in the complex therapy for hemophilia "A" patients", Database HCAPLUS [online], XP002534657, retrieved from STN Database accession No. 2009:502758 abstract & Nanosistemi, Nanomateriali, Nanotekhnologii, vol. 6, No. 2, 2008.
Le Van Mao, Raymond et al. "Mesoporous Aluminosilicates prepared from Zeolites by Treatment with Ammonium Fluorosilicate." J. Mater. Chem. 1993. pp. 679-683. vol. 3, No. 6.
Le et al.: "Recent development in fibres and materials for wound management," Indian Journal of Fibre & Textile Research, 1997.
Li et al.: "Herbs for Promoting Astriction," Chinese Materia Medica Combinations and Applications, Chapter 18, p. 622. 2002.
Lin et al., Synthesis of Hybridized Polyacrylic Acid-Kaolin Material and Its Superwater Absorbent Performance, J. Huaqiao Univ. (Nat. Sci.) 2000-03.
Long et al., Synthesis of Bentonite-superabsorbent Composite, J. Guilin Inst. Tech., 2004-02.
Macrina, VCU's Research Enterprise, Structure and Resources, Oct. 23, 2008.
Manugel® GMB alginate, FMC BioPolymer, Know how. It works. sm Product Specifications, 2011 FMC Corporation.

(56) References Cited

OTHER PUBLICATIONS

Margolis, "Initiation of Blood Coagulation By Glass and Related Surfaces", J. Physiol. (1957) 137, 95-109.

Margolis, J., The Kaolin Clotting Time: A Rapid One-Stage Method for Diagnosis of Coagulation Defects, J. Clin. Pathol 1958, 11, pp. 406-409 (5 pages total).

Medline Maxorb Extra AG Silver Alginate, http://www.medicaldepartmentstore.com/Medline-Maxorb-p/1560.htm (last accessed May 22, 2012).

Miyajima, C., General Information on Alginates and its Applications, Sen'i Gakkaishi (Fibers and Industry), 2009, pp. 444-448, vol. 65, No. 12.

Oh, Seung-Taek et al.: "The Preparation of Plyurethane Foam Combined with pH-sensitive Alginate/Bentonite Hydrogel for Wound Dressings," Fibers and Polymers 2011, vol. 12. No. 2, 159-165.

Okada, et al.: "Preparation of zeolite-coated cordierite honeycombs prepared by an in situ crystallization method", Science and Technology of Advanced Materials 2004 5:479-484.

O'Reilly et al.: "Studies on Coumarin Anticoagulant Drugs—Initiation of Warfarin Therapy Without a Loading Dose", Circulation by the American Heart Association, http://circ.ahajournals.org, 1968, 38, 169-177.

Ore-Medix, Traumastat Hemostatic Bandage, Aug. 7, 2008.

Permanent suspension of Woundstat use, https://email.z-medica.com, Apr. 17, 2009.

Pusateri, et al.: "Application of a Granular Mineral-Based Hemostatic Agent (QuickClot) to Reduce Blood Loss After Grade V Liver Injury in Swine," The Journal of Trauma, Injuary, Infection, and Critical Care, 2004:57 555-562.

Pusateri, et al.: "Effect of a Chitosan-Based Hemostatic Dressing on Blood Loss and Survival in a Model of Sever Henous Hemorrage and Hepatic Injury in Swine," The Journal of Trauma, Injury, Infection, and Critical Care, 2003: 54 177-182.

Qin, et al.: "Water-solubility of chitosan and its antimicrobial activity," Carbohydrate Polymers 63 (2006) 367-374.

Reprinted related contents of U.S. Abstract regarding QuikClot Combat Gauze, Apr. 2009.

Reprinted related contents of US Alaract regarding QuikClot CombatGauze, Sep. 2008.

Revised Pharmaceutical Product Additive Handbook, Yakuji Hosha Inc., Feb. 28, 2007, first printing, p. 41-44 (publication showing well-known technology).

Revised Pharmaceutical Product Additive Handbook, Yakuji Hosha Inc., Feb. 28, 2007, first printing, p. 41-44. (Partial translation).

Ross, et al., "The Kaolin Minerals," J. Amer. Ceramic Soc., vol. 13, issue 3, pp. 151 to 160, Mar. 1930.

Sadler et al.: "Biochemistry and Genetics of Van Willebrand Factor", Annual Review of Biochemistry; 1998. 67:395-424.

Scott Sackinger's Medical Devices Professional Summary dated Mar. 2009.

Segal, H. C. et al., The Effects of Alginate and Non-Alginate Wound Dressings on Blood Coagulation and Platelet Activation, Journal of Biomaterials Applications, Jan. 1998, vol. 12, No. 3, pp. 249-257.

Sinter. (2004). In The New Penquin Dictionary of Science. London: Penguin. Retrieved May 7, 2009, from http://www.credoreference.com/entry/7463549/.

Soine et al., Roger's Inorganic Pharmaceutical Chemistry, Lea & Febiger 1967, p. 462-463 (Aluminum and Aluminum Compounds), [QV744 S683r 1967] total 5 pages.

Stasilon, Wikipedia—definiation 2011.

Tactical Combat Casualty Care Guidelines, Feb. 2009.

The Merck Index; 1989, pp. 1596-1597, abstract 10021.

Top, Ayben et al. "Silver, zinc, and copper exchange in a Na-clinoptilolite and resulting effect on antibacterial activity." Applied Clay Science. 2004. pp. 13-19. vol. 27.

Traditional Chinese Medicine, A Manual from A-Z. Symptoms, Therapy and Herbal Remedies. Springer-Verlag Berlin Heidelberg 2003.

TraumaCure, Innovative Wound Care Products for Wound Care Solutions, Apr. 24, 2009.

U.S. Appl. No. 11/054,918, filed Feb. 9, 2005 including prosecution history.
U.S. Appl. No. 12/555,876, filed Sep. 9, 2009, including prosecution history.
U.S. Appl. No. 13/598,381, filed Aug. 29, 2012, including prosecution history.
U.S. Appl. No. 11/592,477, filed Nov. 2, 2006 including prosecution history.
U.S. Appl. No. 13/595,932, filed Aug. 27, 2012, including prosecution history.
U.S. Appl. No. 11/634,673, filed Dec. 5, 2006 including prosecution history.
U.S. Appl. No. 11/590,427, filed Oct. 30, 2006 including prosecution history.
U.S. Appl. No. 12/417,802, filed Apr. 3, 2009 including prosecution history.
U.S. Appl. No. 13/115,699, filed May 25, 2011 including prosecution history.
U.S. Appl. No. 13/593,310, filed Aug. 23, 2012, including prosecution history.
U.S. Appl. No. 13/911,616, filed Jun. 6, 2013, including prosecution history.
U.S. Appl. No. 12/611,830, filed Nov. 3, 2009, including prosecution history.
U.S. Appl. No. 11/633,687, filed Dec. 4, 2006 including prosecution history.
U.S. Appl. No. 11/654,409, filed Jan. 17, 2007, including prosecution history.
U.S. Appl. No. 11/715,057, filed Mar. 6, 2007 including prosecution history.
U.S. Appl. No. 12/581,782, filed Oct. 19, 2009 including prosecution history.
U.S. Appl. No. 13/682,085, filed Nov. 20, 2012, including prosecution history.
U.S. Appl. No. 13/759,963, filed Feb. 5, 2013, including prosecution history.
U.S. Appl. No. 15/950,832, filed Apr. 11, 2018 including prosecution history.
U.S. Appl. No. 10/939,869, filed Sep. 13, 2004 including prosecution history.
U.S. Appl. No. 12/510,203, filed Jul. 27, 2009 including prosecution history.
U.S. Appl. No. 11/082,716, filed Mar. 16, 2005 including prosecution history.
U.S. Appl. No. 11/303,607, filed Dec. 16, 2005 including prosecution history.
U.S. Appl. No. 11/404,126, filed Apr. 13, 2006 including prosecution history.
U.S. Appl. No. 11/586,968, filed Oct. 25, 2006 including prosecution history.
U.S. Appl. No. 10/939,687, filed Sep. 13, 2004 including prosecution history.
U.S. Appl. No. 12/568,561, filed Sep. 28, 2009 including prosecution history.
U.S. Appl. No. 11/023,869, filed Dec. 27, 2004 including prosecution history.
U.S. Appl. No. 11/584,079, filed Oct. 20, 2006 including prosecution history.
U.S. Appl. No. 11/606,617, filed Nov. 29, 2006 including prosecution history.
U.S. Appl. No. 11/710,106, filed Feb. 22, 2007 including prosecution history.
U.S. Appl. No. 12/101,336, filed Apr. 11, 2008 including prosecution history.
U.S. Appl. No. 12/101,346, filed Apr. 11, 2008 including prosecution history.
U.S. Appl. No. 11/634,531, filed Dec. 6, 2006 including prosecution history.
U.S. Appl. No. 12/140,356, filed Jun. 17, 2008 including prosecution history.
U.S. Appl. No. 12/204,129, filed Sep. 4, 2008 including prosecution history.

(56) References Cited

OTHER PUBLICATIONS

U.S. Appl. No. 11/544,238, filed Oct. 6, 2006 including prosecution history.
U.S. Appl. No. 12/503,481, filed Jul. 15, 2009 including prosecution history.
U.S. Appl. No. 13/240,795, filed Sep. 22, 2011, including prosecution history.
U.S. Appl. No. 14/479,214, filed Sep. 5, 2014 including prosecution history.
U.S. Appl. No. 14/995,592, filed Jan. 14, 2016 including prosecution history.
U.S. Appl. No. 15/641,999, filed Jul. 5, 2017 including prosecution history.
U.S. Appl. No. 15/995,672, filed Jun. 1, 2018 including prosecution history.
U.S. Appl. No. 13/175,380, filed Jul. 1, 2011, including prosecution history.
U.S. Appl. No. 13/922,115, filed Jun. 19, 2013, including prosecution history.
U.S. Appl. No. 15/071,520, filed Mar. 16, 2016, including prosecution history.
U.S. Appl. No. 15/429,935, filed Feb. 10, 2017 including prosecution history.
U.S. Appl. No. 17/179,013, filed Feb. 18, 2021 including prosecution history.
U.S. Appl. No. 12/352,513, filed Jan. 12, 2009 including prosecution history.
U.S. Appl. No. 13/526,431, filed Jun. 18, 2012 including prosecution history.
U.S. Appl. No. 60/668,022, filed Apr. 4, 2005, including prosecution history.
U.S. Appl. No. 60/708,206, filed Aug. 15, 2005, including prosecution history.
U.S. Appl. No. 60/902,738, filed Feb. 21, 2007, including prosecution history.
U.S. Appl. No. 60/955,854, filed Aug. 14, 2007, including prosecution history.
Vitrify—(2001). In Chambers 21st Century Dictionary. London. Chambers Harrap. Retrieved May 7, 2009, from http://www.credoreference.com/entry/1236485/.
Vlok, Marie E.: "Kaolin poultice", Manual of Nursing, vol. 1, Basic Nursing, revised ninth edition, p. 269. Copyright Juta & Co, Ltd., Lansdowne, South Africa, first published 1962.
Voet, Donald & Judith: "Molecular Physiology", Biochemistry, p. 1087-1096, vol. 64, 1990, John Wiley & Sons.
Wagner, Holly, "Topical Oxygen Helps Hard-To-Heal Wounds Heal Faster and Better," Jan. 28, 2003, obtained from http://researchnews.osu.edu/archive/oxywound.htm.
Ward, et al., The Journal of Trauma Injury, Infection, and Critical Care, Comparison of a New Hemostatic Agent to Current Combat Hemostatic Agents in a Swine Model of Lethal Extremity Arterial Hemorrhage, Aug. 2007, pp. 276-284.
Ward, Declaration and CV, signed Jul. 19, 2012.
Webster's Dictionary definition of "expose" (1993).
Wound Stat, http://shadowspear.com/vb/showthread.php?t=16586 dated Dec. 22, 2008, last accessed Apr. 16, 2009.
WoundStat found to be potentially hazardous, Army News, news from Iraq . . . , http://armytimes.com/news/2009/04/army_woundstat_042009w/, posted Apr. 20, 2009, last accessed Apr. 20, 2009.
Wright, J. Barry et al.: "Wound management in an era of increasing bacterial antibiotic resistance: A role for topical silver treatment", American Journal of Infection Control, vol. 26 (6), 1998, pp. 572-577.
Wright, J.K et al. "Thermal Injury Resulting from Application of a GranularMineral Hemostatic Agent." The Journal of Trauma Injury, Infection, and Critical Care. 2004. pp. 224-230. vol. 57, No. 2.
Wu, Jing-Nuan, "An Illustrated Chinese Materia Medica," Oxford University Press, Inc. 2005 (13 pages).
Xinrong, Traditional Chinese Medicine, A Manual from A-Z, Symptoms, Therapy and Herbal Remedies, [ISBN 3 540 42846 1], p. 470 (total 3 pages), Springer-Verlag Berlin Heidelberg 2003.
Yanchi, The Essential Book of Traditional Chinese Medicine, vol. 2: Clinical Practice, p. 155-157 (Traditional Chinese Prescriptions), , 142-143 (Chinese Medicinal Herbs) total 8 pages. [ISBN 0 231 06518 3 9v.2] 1988.
Yanchi, Liu: "Drug Forms: Their Administration and Actions," The Essential Book of Traditional Chinese Medicine 7, vol. 2: Clinical Practice. 1988.
Z-Medica Corporation 510(k) Summary, QuikClot eX, Oct. 4, 2007.
Cease and Desist Letter from Z-Medica, LLC to Protégé Biomedical, LLC, dated Oct. 10, 2018 (21 pages).
Plaintiff Protégé Biomedical, LLC's Complaint, dated Nov. 19, 2018 ("Complaint"), filed against Defendant Z-Medica, LLC, in Case No. 0:18-cv-03227 (12 pages).
Plaintiff Protégé Biomedical, LLC's First Amended Complaint (and Exhibits A and B), dated Jan. 25, 2019 ("First Amended Complaint"), in Case No. 0:18-cv-03227 (156 pages).
Defendant Z-Medica, LLC's Motion to Dismiss Plaintiff's First Amended Complaint, dated Feb. 7, 2019 in Case No. 0:18-cv-03227 (2 pages).
Defendant Z-Medica, LLC's Memorandum of Law in Support of Defendant's Motion to Dismiss Plaintiff's First Amended Complaint, dated Feb. 7, 2019 in Case No. 0:18-cv- 03227 (35 pages).
Declaration of Dina Dubey submitted with Memorandum of Law in Support of Defendant's Motion to Dismiss Plaintiff's First Amended Complaint, dated Feb. 7, 2019 in Case No. 0:18-cv-03227 (5 pages).
Plaintiff Protégé Biomedical, LLC's Response Memorandum of Law in Opposition to Defendant's Motion to Dismiss Under Fed. R. Civ. P. 12(B)(2) and 12(B)(6), dated Feb. 28, 2019, in Case No. 0:18-cv-03227 (48 pages).
Defendant Z-Medica, LLC's Reply in Support of Defendant's Motion to Dismiss Plaintiff's First Amended Complaint, dated Mar. 14, 2019 in Case No. 0:18-cv-03227 (20 pages).
Declaration of Dina Dubey submitted with Reply in Support of Defendant's Motion to Dismiss Plaintiff's First Amended Complaint, dated Mar. 14, 2019 in Case No. 0:18-cv-03227 (2 pages).
Plaintiff Protégé Biomedical, LLC's Motion for Injunctive Relief and Expedited Handling of the Case, dated Dec. 12, 2018, in Case No. 0:18-cv-03227.
Plaintiff Protégé Biomedical, LLC's Memorandum of Law in Support of Protégé Biomedical's Motion for Injunctive Relief and Expedited Handling of the Case, dated Dec. 12, 2018, in Case No. 0:18-cv-03227.
Declaration of Susan Wuollett submitted with Memorandum of Law in Support of Protégé Biomedical's Motion for Injunctive Relief and Expedited Handling of the Case, dated Dec. 12, 2018, in Case No. 0:18-cv-03227 (8 pages).
Plaintiff Protégé Biomedical, LLC's Notice of Withdrawal of Plaintiff's Motion for Injunctive Relief Filed Dec. 12, 2018 Without Prejudice, dated Jan. 14, 2019, in Case No. 0:18-cv-03227 (3 pages).
A Rule 26(f) Pretrial Conference Report and its Exhibits, dated Feb. 26, 2019, in Case No. 0:18-cv-03227.
Pretrial Scheduling Order, Dated Filed Mar. 26, 2019 in Case 0:18-cv-03227-JRT-HB; pp. 1 19.
Defendant Z-Medica, LLC's Memorandum in Support of D's First Motion to Compel, dated Apr. 22, 2019, in Case No. 0:18-cv-03227 (32 pages).
Dec of Charles Nauen in Support of Defendant Z-Medica, LLC's Memorandum in Support of D's First Motion to Compel, dated Apr. 22, 2019, in Case No. 0:18-cv-03227 (2 pages).
Exhibits A-C for Dec of Charles Nauen in Support of Defendant Z-Medica, LLC's Memorandum in Support of D's First Motion to Compel, dated Apr. 22, 2019, in Case No. 0:18-cv-03227 (73 pages).
Exhibit D for Dec of Charles Nauen in Support of Defendant Z-Medica, LLC's Memorandum in Support of D's First Motion to Compel, dated Apr. 22, 2019, in Case No. 0:18-cv-03227 (31 pages).

(56) References Cited

OTHER PUBLICATIONS

Exhibit E for Dec of Charles Nauen in Support of Defendant Z-Medica, LLC's Memorandum in Support of D's First Motion to Compel, dated Apr. 22, 2019, in Case No. 0:18-cv-03227 (6 pages).
Exhibit F for Dec of Charles Nauen in Support of Defendant Z-Medica, LLC's Memorandum in Support of D's First Motion to Compel, dated Apr. 22, 2019, in Case No. 0:18-cv-03227 (16 pages).
Exhibit G for Dec of Charles Nauen in Support of Defendant Z-Medica, LLC's Memorandum in Support of D's First Motion to Compel, dated Apr. 22, 2019, in Case No. 0:18-cv-03227 (55 pages).
Plaintiff Protégé Biomedical, LLC's Motion to Compel, dated Apr. 22, 2019, in Case No. 0:18-cv-03227 (21 pages).
Dec of Laura Conley in Support of Plaintiff Protégé Biomedical, LLC's Motion to Compel, dated Apr. 22, 2019, in Case No. 0:18-cv-03227 (3 pages).
Exhibit C for Dec of Laura Conley in Support of Plaintiff Protégé Biomedical, LLC's Motion to Compel, dated Apr. 22, 2019, in Case No. 0:18-cv-03227 (7 pages).
Exhibit D for Dec of Laura Conley in Support of Plaintiff Protégé Biomedical, LLC's Motion to Compel, dated Apr. 22, 2019, in Case No. 0:18-cv-03227 (31 pages).
Exhibit E for Dec of Laura Conley in Support of Plaintiff Protégé Biomedical, LLC's Motion to Compel, dated Apr. 22, 2019, in Case No. 0:18-cv-03227 (30 pages).
Exhibit F for Dec of Laura Conley in Support of Plaintiff Protégé Biomedical, LLC's Motion to Compel, dated Apr. 22, 2019, in Case No. 0:18-cv-03227 (20 pages).
Exhibit I for Dec of Laura Conley in Support of Plaintiff Protégé Biomedical, LLC's Motion to Compel, dated Apr. 22, 2019, in Case No. 0:18-cv-03227 (3 pages).
Exhibit J for Dec of Laura Conley in Support of Plaintiff Protégé Biomedical, LLC's Motion to Compel, dated Apr. 22, 2019, in Case No. 0:18-cv-03227 (3 pages).
Exhibit K for Dec of Laura Conley in Support of Plaintiff Protégé Biomedical, LLC's Motion to Compel, dated Apr. 22, 2019, in Case No. 0:18-cv-03227 (16 pages).
Exhibit L for Dec of Laura Conley in Support of Plaintiff Protégé Biomedical, LLC's Motion to Compel, dated Apr. 22, 2019, in Case No. 0:18-cv-03227 (6 pages).
Exhibit N for Dec of Laura Conley in Support of Plaintiff Protégé Biomedical, LLC's Motion to Compel, dated Apr. 22, 2019, in Case No. 0:18-cv-03227 (5 pages).
Defendant Z-Medica, LLC's Opposition to Plaintiff's Motion to Compel, dated Apr. 23, 2019, in Case No. 0:18-cv-03227 (3 pages).
Plaintiff Protégé Biomedical, LLC's Combined Response Reply Brief on Motions to Compel, dated Apr. 30, 2019, in Case No. 0:18-cv-03227 (15 pages).
Plaintiff Protégé Biomedical, LLC's Interrogatory Responses, dated Apr. 30, 2019, in Case No. 0:18 cv-03227 (51 pages).
Plaintiff Protégé Biomedical, LLC's Memorandum in Support of Leave to Amend Complaint, dated May 3, 2019, in Case No. 0:18-cv-03227 (6 pages).
Dec of Joseph Balthazor for in Support of Plaintiff Protégé Biomedical, LLC's Memorandum in Support of Leave to Amend Complaint, dated May 3, 2019, in Case No. 0:18-cv-03227 (3 pages).
Plaintiff Protégé Biomedical, LLC's Second Amended Complaint, dated May 3, 2019, in Case No. 0:18 cv-03227 (48 pages).
Order Approving Stipulation To Stay Pending Ruling on Motion to Dismiss, dated May 27, 2019, in Case No. 0:18-cv-03227 (1 page).
Opinion and Order Regarding Defendant Z-Medica's Motion to Dismiss, dated Jul. 24, 2019, in Case No. 0:18 cv-03227 (29 pages).
Defendant Z-Medica LLC's Answer to Amended Complaint, dated Aug. 21, 2019, in Case No. 0:18 cv-03227 (67 pages).
Plaintiff Protege Biomedical, LLC's Reply and Affirmative Defenses, dated Sep. 11, 2019, in Case No. 0:18-cv-03227 (8 pages).
Settlement Conference Minutes, dated Sep. 18, 2019, in Case No. 0:18-cv-03227 (2 pages).

Protégé Biomedica, LLC Invalidity Contentions of Z-Medica, LLC U.S. Pat. No. 10,086,106, in Case No. 0:18-cv-03227, dated Oct. 11, 2019 (363 pages).
Defendant Z-Medica LLC's Motion for Leave to Amend Initial Infringement Claim Charts date Nov. 8, 2019, in Case No. 0:18 cv-03227 (2 pages).
Joint Claim Construction Statement, dated Nov. 13, 2019, in Case No. 0:18-cv-03227 and Exhibits A-F thereof (28 pages).
Plaintiff Protege Biomedical, LLC's Response Memorandum in Opposition to Z-Medica, LLC's Motion for Leave to Amend Initial Infringement Claim Charts, dated Nov. 15, 2019, in Case No. 0:18-cv-03227 (8 pages).
Declaration of Andrew S. Dosdall in Support of Defendant's Motion for Leave to Amend initial Infringement Claim Charts, dated Nov. 15, 2019 (2 pages).
Statement Regarding Exhibit A Accompanying Declaration of Andrew S. Dosdall, dated Nov. 15, 2019 (2 pages).
Defendant Z-Medica LLC's Response to Protégé Biomedical, LLC's Invalidity Contentions Regarding U.S. Pat. No. 10,086,106, in Case No. 0:18-cv-03227, (251 pages).
Plaintiff Protégé Biomedical, LLC's Motion for Preliminary Injunction, dated Dec. 12, 2018, in Case No. 0:18-cv-03227 (4 pages).
Plaintiff Protégé Biomedical, LLC's Memo in Support of Preliminary Injunction, dated Dec. 12, 2018, in Case No. 0:18-cv-03227 (34 pages).
Joint Claim Construction Statement, dated Jan. 15, 2020, in Case No. 0:18-cv-03227 (11 pages).
Counterclaim Plaintiff Z-Medica, LLC's Opening Claim Construction Brief, dated Jan. 27, 2020, in Case No. 0:18-cv-03227 (17 pages).
Declaration of Ali Razai and Exhibits in Support of Counterclaim Plaintiff Z-Medica, LLC's Claim Construction Brief, dated Jan. 27, 2020, in Case No. 0:18-cv-03227 (167 pages).
Declaration of Douglas Loy and Exhibits in Support of Counterclaim Plaintiff Z-Medica, LLC's Claim Construction Brief, dated Jan. 27, 2020, in Case No. 0:18-cv-03227 (44 pages).
Plaintiff Protégé Biomedical, LLC's Opening Claim Construction Brief, dated Jan. 27, 2020, in Case No. 0:18-cv-03227 (39 pages).
Declaration of Andrew Dosdall and Exhibits in Support of Plaintiff Protégé Biomedical, LLC's Opening Claim Construction Brief, dated Jan. 27, 2020, in Case No. 0:18-cv-03227 (88 pages).
Plaintiff Protégé Biomedical, LLC's Motion to Compel, dated Jan. 30, 2020, in Case No. 0:18-cv-03227 (2 pages).
Plaintiff Protégé Biomedical, LLC's Memorandum in Support of Motion to Compel, dated Jan. 30, 2020, in Case No. 0:18-cv-03227 (20 pages).
Declaration of Balthazor and Exhibits in Support of Plaintiff Protégé Biomedical, LLC's Motion to Compel, dated Jan. 30, 2020, in Case No. 0:18-cv-03227 (25 pages).
Defendant Z-Medica, LLC's Motion to Compel, dated Jan. 31, 2020, in Case No. 0:18-cv-03227 (2 pages).
Defendant Z-Medica, LLC's Memorandum in Support of Motion to Compel, dated Jan. 30, 2020, in Case No. 0:18-cv-03227 (35 pages).
Declaration of Charles Nauen and Exhibits in Support of Defendant Z-Medica, LLC's Motion to Compel, dated Jan. 30, 2020, in Case No. 0:18-cv-03227 (25 pages).
Defendant Z-Medica, LLC's Opposition to P's Motion to Compel, dated Feb. 6, 2020, in Case No. 0:18-cv-03227 (48 pages).
Plaintiff Protégé Biomedical, LLC's Opposition to D's Motion to Compel, dated Feb. 7, 2020, in Case No. 0:18-cv-03227 (26 pages).
Exhibit for Plaintiff Protégé Biomedical, LLC's Opposition to D's Motion to Compel, dated Feb. 7, 2020, in Case No. 0:18-cv-03227 (26 pages).
Plaintiff Protégé Biomedical, LLC's Responsive Claim Construction Brief, dated Feb. 10, 2020, in Case No. 0:18-cv-03227 (10 pages).
Counterclaim Plaintiff Z-Medica, LLC's Responsive Claim Construction Brief, dated Feb. 10, 2020, in Case No. 0:18-cv-03227 (35 pages).
Second Declaration of Ali Razai in Support of Counterclaim Plaintiff Z-Medica, LLC's Responsive Claim Construction Brief, dated Feb. 10, 2020, in Case No. 0:18-cv-03227 (4 pages).

(56) References Cited

OTHER PUBLICATIONS

Declaration of Andrew Dosdall and Exhibits in Opposition of Defendant Z-Medica, LLC's Second Motion to Compel, dated Feb. 18, 2020, in Case No. 0:18-cv-03227 (12 pages).
Letter to Magistrate Judge Regarding Defendant Z-Medica, LLC's Second Motion to Compel dated Feb. 21, 2020, in Case No. 0:18-cv-03227 (3 pages).
Third Amended pretrial Case Management Order, dated Feb. 21, 2020, in Case No. 0:18-cv-03227 (22 pages).
Plaintiff Protégé Biomedical, LLC's Memorandum of Law in Support of Leave to Amend First Amended Complaint, dated Mar. 2, 2020, in Case No. 0:18-cv-03227 (15 pages).
Declaration Balthazor of in Support of Plaintiff Protégé Biomedical, LLC's Memorandum of Law in Support of Leave to Amend First Amended Complaint dated Mar. 2, 2020, in Case No. 0:18-cv-03227 (187 pages).
Exhibit A to Balthazor Declaration for Plaintiff Protégé Biomedical, LLC's Second Amended Complaint, dated Mar. 3, 2020, in Case No. 0:18-cv-03227 (183 pages).
Defendant Z-Medica, LLC's Partial Opposition to P's Motion for Leave to Amend, dated Mar. 20, 2020, in Case No. 0:18-cv-03227 (36 pages).
Declaration of Charles N. Nauen and Exhibits in Support of Defendant Z-Medica, LLC's Partial Opposition to P's Motion for Leave to Amend, dated Mar. 20, 2020, in Case No. 0:18-cv-03227 (15 pages).
Redacted Exhibit C of Declaration of Charles N. Nauen in Support of Defendant Z-Medica, LLC's Partial Opposition to P's Motion for Leave to Amend, dated Mar. 20, 2020, in Case No. 0:18-cv-03227 (8 pages).
Statement of Charles Nauen for Defendant Z-Medica, LLC that Entire Documents are Confidential Or Impracticable to Redact, dated Mar. 20, 2020, in Case No. 0:18-cv-03227 (2 pages).
Proposede Order Denying P's Motion to Leave to Amend, dated Mar. 20, 2020, in Case No. 0:18-cv-03227 (15 pages).
Stipulation to Amend Schedule, dated Mar. 27, 2020, in Case No. 0:18-cv-03227 (4 pages).
Amended Joint Claim Construction Statement, dated Mar. 27, 2020, in Case No. 0:18-cv-03227 (5 pages).
Joint Claim Construction Letter, dated Mar. 27, 2020, in Case No. 0:18-cv-03227 (2 pages).
Order to Amend Schedule, dated Mar. 30, 2020, in Case No. 0:18-cv-03227 (2 pages).
Plaintiff Protégé Biomedical, LLC's Objections to the Magistrate Judge's Mar. 17, 2020 Order On Its Motion to Compel the Production of Privileged Documents, dated Mar. 31, 2020, in Case No. 0:18-cv-03227 (16 pages).
Declaration of Laura Conley and Exhibits in Support of Plaintiff Protégé Biomedical, LLC's Objections to the Magistrate Judge's Mar. 17, 2020 Order On Its Motion to Compel the Production of Privileged Documents, dated Mar. 31, 2020, in Case No. 0:18-cv-03227 (19 pages).
Declaration of Philip O'Beirne and Exhibits in Support of Defendant Z-Medica, LLC's Submission for Attorneys' Fees, dated Mar. 31, 2020, in Case No. 0:18-cv-03227 (10 pages).
Plaintiff Protégé Biomedical, LLC's Reply Memorandum In Support of Leave to Amend, dated Apr. 2, 2020, in Case No. 0:18-cv-03227 (35 pages).
Order Regarding Payment of D's Attorney Fees, dated Apr. 6, 2020, in Case No. 0:18-cv-03227 (2 pages).
Defendant Z-Medica, LLC's Sur-Reply in Support Partial Opposition to P's Motion for Leave to Amend, dated Apr. 6, 2020, in Case No. 0:18-cv-03227 (18 pages).
Declaration of Charles N. Nauen and Exhibits in Support of Defendant Z-Medica, LLC's Sur-Reply, dated Apr. 6, 2020, in Case No. 0:18-cv-03227 (1 page).
Declaration of Jack Y. Perry in Support of Plaintiff Protégé Biomedical, LLC's in Support of P's Motion for Leave to Amend First Amended Complaint, dated Apr. 13, 2020, in Case No. 0:18-cv-03227 (1 page).
Declaration of Philip O'Beirne in Support of Defendant Z-Medica, LLC's Opposition to P's Motion for Leave to Amend, dated Apr. 14, 2020, in Case No. 0:18-cv-03227 (3 pages).
Redacted Response by Defendant Z-Medica, LLC's in Response to P's Motions of Mar. 17, 2020, dated Apr. 14, 2020, in Case No. 0:18-cv-03227 (17 pages).
Supplemental Declaration of Jack Y. Perry in Support of Plaintiff Protégé Biomedical, LLC's in Support of P's Motion for Leave to Amend First Amended Complaint, dated Apr. 15, 2020, in Case No. 0:18-cv-03227 (3 pages).
Plaintiff Protégé Biomedical, LLC's Request for Oral Hearing, dated Apr. 17, 2020, in Case No. 0:18-cv-03227 (2 pages).
Plaintiff Protégé Biomedical, LLC's Objections to the Magistrate Judge's May 26, 2020 Order On Its Motion to for leave to Amend its First Amended Complaint, dated Jun. 9, 2020, in Case No. 0:18-cv-03227 (16 pages).
Order denying Plaintiff's Motion to Compel Discovery, and granting Defendant's request for sanctions as to the cost of Z-Medica's reasonable fees and expenses incurred in opposing the motion, but denied as to any further relief, dated Mar. 17, 2020, in Case No. 0:18-cv-03227 (13 pages).
Order on Stipulation to Amend Case Schedule, dated Jun. 8, 2020, in Case No. 0:18-cv-03227 (2 pages).
Declaration of Charles N. Nauen (and Exhibits) in Support of Defendant's Opposition to Protégé's Third Motion to Compel, dated Jun. 15, 2020, in Case No. 0:18-cv-03227 (42 pages).
Defendant Z-Medica's Response to Protégé's Objections to the Magistrate Judge's Order On Its Motion to for leave to Amend its First Amended Complaint, dated Jun. 23, 2020, in Case No. 0:18-cv-03227 (15 pages).
Memorandum Opinion and Order Affirming Magistrate Judge Order and overruling 316 Objection by Protege Biomedical, LLC, dated Jul. 6, 2020, in Case No. 0:18-cv-03227 (8 pages).
Final Consent Judgment and Permanent Injunction, dated Aug. 13, 2020, in Case No. 0:18-cv-03227 (4 pages).
A Docket Report from Mar. 5, 2019, in Case No. 0:18-cv-03227.
A Docket Report from May 6, 2019, in Case No. 0:18-cv-03227.
A Docket Report from Sep. 16, 2019, in Case No. 0:18-cv-03227 (18 pages).
A Docket Report from Dec. 16, 2019, in Case No. 0:18-cv-03227 (25 pages).
A Docket Report from Mar. 13, 2020, in Case No. 0:18-cv-03227 (33 pages).
A Docket Report from Apr. 22, 2020, in Case No. 0:18-cv-03227 (33).
A Docket Report from Jul. 20, 2020, in Case No. 0:18-cv-03227 (37 pages).
A Docket Report from Sep. 9, 2020, in Case No. 0:18-cv-03227 (38 pages).
"Calcium alginate—Wikipedia," wikipedia, Jan. 24, 2023, XP93017476, retrieved from the internet: ULR:Https://en.wikipedia.org/wiki/Calcium_alginate [retrieved on Jan. 25, 2023].

HEMOSTATIC DEVICES

CROSS-REFERENCE TO RELATED APPLICATIONS

This application is a continuation of U.S. patent application Ser. No. 17/178,047, filed Feb. 17, 2021, which is a continuation of U.S. patent application Ser. No. 15/841,843, filed Dec. 14, 2017, and issued as U.S. Pat. No. 10,960,101, entitled "Clay-Based Hemostatic Agents," which is a continuation of U.S. patent application Ser. No. 15/090,072, filed Apr. 4, 2016, and issued as U.S. Pat. No. 9,867,898, entitled "Clay-Based Hemostatic Agents," which is a continuation of U.S. patent application Ser. No. 14/185,873, filed Feb. 20, 2014, and issued as U.S. Pat. No. 9,333,117, entitled "Clay-Based Hemostatic Agents and Devices for the Delivery Thereof," which is a continuation of U.S. patent application Ser. No. 13/759,963, filed Feb. 5, 2013, and issued as U.S. Pat. No. 9,078,782, entitled "Hemostatic Fibers and Strands," which is a continuation of U.S. patent application Ser. No. 13/682,085, filed Nov. 20, 2012, and issued as U.S. Pat. No. 8,846,076, entitled "Hemostatic Sponge," which is a continuation of U.S. patent application Ser. No. 13/363,270, filed Jan. 31, 2012, and issued as U.S. Pat. No. 8,343,537, entitled "Clay-Based Hemostatic Agents and Devices for the Delivery Thereof," which is a continuation of U.S. patent application Ser. No. 12/581,782, filed Oct. 19, 2009, and issued as U.S. Pat. No. 8,114,433, entitled "Clay-Based Hemostatic Agents and Devices for the Delivery Thereof," which is a continuation of U.S. patent application Ser. No. 11/715,057, filed Mar. 6, 2007, and issued as U.S. Pat. No. 7,604,819, entitled "Clay-Based Hemostatic Agents and Devices for the Delivery Thereof," which is a continuation-in-part application of U.S. patent application Ser. No. 11/590,427, filed Oct. 30, 2006, and issued as U.S. Pat. No. 7,968,114, entitled "Clay-Based Hemostatic Agents and Devices for the Delivery Thereof," which claims the benefit of U.S. Provisional Patent Application Ser. No. 60/808,618, filed May 26, 2006, entitled "Blood Clotting Compound" and U.S. Provisional Patent Application Ser. No. 60/810,447, filed Jun. 1, 2006, entitled "Hemostatic Device with Oxidized Cellulose Pad." The contents of all of the above-referenced applications are incorporated herein by reference in their entireties.

BACKGROUND OF THE INVENTION

Field of the Invention

The present invention relates generally to agents and devices for promoting hemostasis and, more particularly, to clay-based hemostatic agents and devices incorporating such agents for the delivery thereof to bleeding wounds.

Description of the Related Art

Blood is a liquid tissue that includes red cells, white cells, corpuscles, and platelets dispersed in a liquid phase. The liquid phase is plasma, which includes acids, lipids, solubilized electrolytes, and proteins. The proteins are suspended in the liquid phase and can be separated out of the liquid phase by any of a variety of methods such as filtration, centrifugation, electrophoresis, and immunochemical techniques. One particular protein suspended in the liquid phase is fibrinogen. When bleeding occurs, the fibrinogen reacts with water and thrombin (an enzyme) to form fibrin, which is insoluble in blood and polymerizes to form clots.

In a wide variety of circumstances, animals, including humans, can be wounded. Often bleeding is associated with such wounds. In some circumstances, the wound and the bleeding are minor, and normal blood clotting functions in addition to the application of simple first aid are all that is required. Unfortunately, however, in other circumstances substantial bleeding can occur. These situations usually require specialized equipment and materials as well as personnel trained to administer appropriate aid. If such aid is not readily available, excessive blood loss can occur. When bleeding is severe, sometimes the immediate availability of equipment and trained personnel is still insufficient to stanch the flow of blood in a timely manner.

Moreover, severe wounds can often be inflicted in remote areas or in situations, such as on a battlefield, where adequate medical assistance is not immediately available. In these instances, it is important to stop bleeding, even in less severe wounds, long enough to allow the injured person or animal to receive medical attention.

In an effort to address the above-described problems, materials have been developed for controlling excessive bleeding in situations where conventional aid is unavailable or less than optimally effective. Although these materials have been shown to be somewhat successful, they are sometimes not effective enough for traumatic wounds and tend to be expensive. Furthermore, these materials are sometimes ineffective in some situations and can be difficult to apply as well as remove from a wound.

Additionally, or alternatively, the previously developed materials can produce undesirable side effects. For example, one type of prior art blood clotting material is generally a powder or a fine particulate in which the surface area of the material often produces an exothermic reaction upon the application of the material to blood. Oftentimes excess material is unnecessarily poured onto a wound, which can exacerbate the exothermic effects. Depending upon the specific attributes of the material, the resulting exothermia may be sufficient to cause discomfort to or even burn the patient. Although some prior art patents specifically recite the resulting exothermia as being a desirable feature that can provide clotting effects to the wound that are similar to cauterization, there exists the possibility that the tissue at and around the wound site may be undesirably impacted.

Furthermore, to remove such materials from wounds, irrigation of the wound is often required. If an amount of material is administered that causes discomfort or burning, the wound may require immediate flushing. In instances where a wounded person or animal has not yet been transported to a facility capable of providing the needed irrigation, undesirable effects or over-treatment of the wound may result.

Bleeding can also be a problem during surgical procedures. Apart from suturing or stapling an incision or internally bleeding area, bleeding is often controlled using a sponge or other material used to exert pressure against the bleed site and/or absorb the blood. However, when the bleeding becomes excessive, these measures may not be sufficient to stop the blood flow. Moreover, any highly exothermic bleed-control material may damage the tissue surrounding the bleed site and may not be configured for easy removal after use.

Based on the foregoing, it is a general object of the present invention to provide a hemostatic agent that overcomes or improves upon the drawbacks associated with the prior art.

It is also a general object of the present invention to provide devices capable of applying such hemostatic agents.

SUMMARY OF THE INVENTION

According to one aspect, the present invention resides in a device for promoting the clotting of blood, thereby controlling bleeding. The device comprises a clay material in particle form and a receptacle for containing the clay material. At least a portion of the receptacle is defined by a mesh having openings therein such that when the device is applied to a bleed site, the particles of clay come into contact with blood through the openings.

According to another aspect, the present invention resides in another device capable of providing a hemostatic effect on a bleeding wound to control blood flow from the wound. The device comprises a gauze substrate and a clay material disposed on the gauze substrate. Upon the application of the device to the bleeding wound, at least a portion of the clay material comes into contact with the blood to cause the hemostatic effect.

According to another aspect, the present invention resides in a bandage that can be applied to a bleeding wound to promote the clotting of blood, thereby controlling bleeding. The bandage comprises a substrate, a mesh mounted on the substrate, and particles of a clay material retained in the mesh. The mesh is defined by a plurality of members arranged to define openings that allow for the flow of blood into the mesh and into the clay material, thereby producing a clotting effect.

According to another aspect, the present invention resides in a hemostatic sponge that can be applied to a bleeding wound to clot blood and control bleeding. Such a sponge comprises a substrate, a hemostatic material disposed on a first surface of the substrate, and a release agent disposed on a second surface of the substrate. The release agent is disposed on the wound-contacting surface of the substrate to inhibit the adherence of the sponge to the wound tissue after clot formation. When treating a bleeding wound, application of the hemostatic sponge causes at least a portion of the hemostatic material to come into contact with blood through the release agent and through the substrate.

According to yet another aspect, the present invention resides in other forms of hemostatic sponges. In such forms the hemostatic sponge may comprise a film and a hemostatic material incorporated into the film; a substrate, a hemostatic material disposed on the substrate, and a film disposed over the hemostatic material; or a hemostatic material sandwiched between two substrates.

According to yet another aspect, the present invention resides in a hemostatic device for promoting the clotting of blood, thereby controlling bleeding. The device has a gauze substrate, a clay material disposed on the gauze substrate, and also a polyol such as glycerol or the like disposed on the gauze substrate to bind the clay material. When the device is used to treat a bleeding wound, at least a portion of the clay material comes into contact with blood emanating from the wound to cause the clotting.

According to yet another aspect, the present invention resides in a bandage that can be applied to a bleeding wound to promote the clotting of blood, thereby controlling bleeding. The bandage has a flexible substrate and a gauze substrate mounted thereon. The gauze substrate includes a clay material and a polyol. When the bandage is used to treat a bleeding wound, applying the bandage to the wound causes at least a portion of the clay material to come into contact with blood emanating from the wound.

According to still another aspect, the present invention resides in hemostatic sponges. One type of sponge has a gauze substrate and a dispersion of hemostatic material and a polyol on a first surface of the substrate. When this sponge is used to treat a bleeding wound, applying the sponge causes at least a portion of the hemostatic material to come into contact with blood. Another type of sponge has first and second substrates. A hemostatic material is dispersed in the polyol and applied to the first substrate, and the second substrate is placed on the hemostatic material dispersed in the polyol. When this sponge is used to treat a bleeding wound, applying the sponge causes at least a portion of the hemostatic material to come into contact with blood through at least one of the substrates.

An advantage of the present invention is that unlike other materials, such as, for example zeolites, the clay component produces no exothermic reaction with blood. Eliminating the generation of heat at a wound site is useful in minimizing discomfort and/or further injury to a patient and may be especially useful in the treatment of certain patients such as pediatric or geriatric patients or when the wound being treated is in a particularly sensitive or delicate area.

Another advantage is that the clay can be finely divided and deposited on a multitude of surfaces, thereby facilitating its use as a component in a variety of blood control devices. In particular, the clay can be used in particle form (e.g., retained in a mesh or in a film), or it can be used in powder form (e.g., deposited on a fibrous substrate to form a gauze or a sponge). In any embodiment, the efficacy of the clay in promoting hemostasis at a wound site is improved over similar agents that can be used only in one form (e.g., as particles of a particular size) to limit undesirable side effects such as excessive exothermic reactions.

Still another advantage of the present invention is that the devices and agents of the present invention are easily applied to open wounds. Particularly when the hemostatic agent is retained in a mesh or similar device, or when it is incorporated into a woven structure to form a gauze, the device can be readily removed from a sterilized packaging and placed or held directly at the points from which blood emanates to cause clotting.

One advantage of the use of a polyol such as glycerol in conjunction with clay (or any other hemostatic agent) is that dust oftentimes associated with the clay (or other hemostatic agent) is suppressed. Because of its low volatility, glycerol, for example, does not readily evaporate. Because it does not readily evaporate, the generation of clay dust when the clay is dispersed in the glycerol is mitigated. Mitigating or suppressing the dust means that more hemostatic material is available for blood clotting purposes.

Another advantage of the use of a polyol in conjunction with clay (or other hemostatic agent) is that the undesirable adhesion of the sponge to the wound is reduced. Accordingly, the sponge or other device can be easily removed from a wound without breaking a newly formed blood clot.

DETAILED DESCRIPTION OF THE PREFERRED EMBODIMENT

Figure 1:
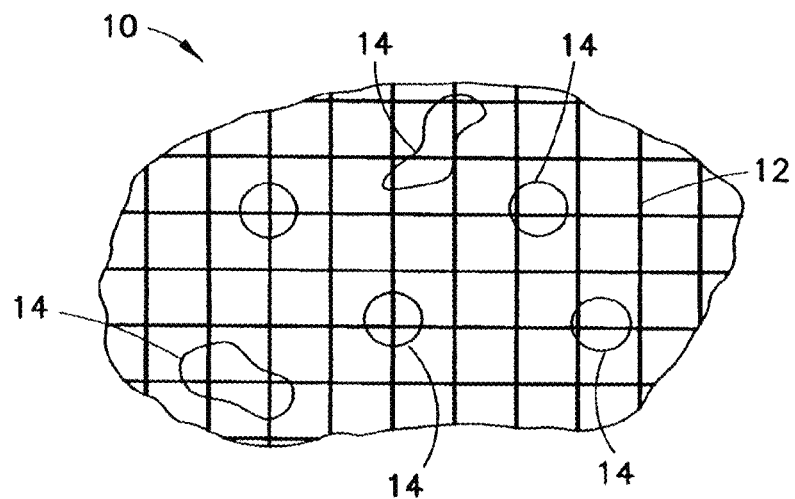
FIG. 1 is a schematic representation of a mesh structure of a blood clotting device of the present invention.

Disclosed herein are hemostatic devices and hemostatic agents that are applicable to bleeding wounds to promote hemostasis. The hemostatic agents generally include clay materials or other silica-based materials that, when brought into contact with a bleeding wound, can minimize or stop blood flow by absorbing at least portions of the liquid phases of the blood, thereby facilitating clotting. The present invention is not limited to clay, however, as other materials such as bioactive glasses, biological hemostats, molecular sieve materials, diatomaceous earth, combinations of the foregoing, and the like are within the scope of the present invention and can be used in conjunction with the clay or separately as a hemostatic agent.

As used herein, the term "clay" refers to a crystalline form of hydrated aluminum silicate. The crystals of clay are irregularly shaped and insoluble in water. The combination of some types of clay with water may produce a mass having some degree of plasticity. Depending upon the type of clay, the combination thereof with water may produce a colloidal gel having thixotropic properties.

In one preferred embodiment of the present invention, the clay material is kaolin, which includes the mineral "kaolinite." Although the term "kaolin" is used hereinafter to describe the present invention, it should be understood that kaolinite may also be used in conjunction with or in place of kaolin. The present invention is also not limited with regard to kaolin or kaolinite, however, as other materials are within the scope of the present invention. Such materials include, but are not limited to, attapulgite, bentonite, combinations of the foregoing, combinations of the foregoing with kaolin and/or diatomaceous earth, and the like.

As used herein, the term "kaolin" refers to a soft, earthy aluminosilicate clay (and, more specifically, to a dioctahedral phyllosilicate clay) having the chemical formula $Al_2Si_2O_5(OH)_4$. Kaolin is a naturally occurring layered silicate mineral having alternating tetrahedral sheets and octahedral sheets of alumina octahedra linked via the oxygen atoms of hydroxyl groups. Kaolin comprises about 50% alumina, about 50% silica, and trace impurities.

More preferably, the clay is Edgar's plastic kaolin (hereinafter "EPK"), which is a water-washed kaolin clay that is mined and processed in and near Edgar, Fla. Edgar's plastic kaolin has desirable plasticity characteristics, is castable, and when mixed with water produces a thixotropic slurry.

The kaolin material of the present invention may be mixed with or otherwise used in conjunction with other materials to provide additional clotting functions and/or improved efficacy. Such materials include, but are not limited to, magnesium sulfate, sodium metaphosphate, calcium chloride, dextrin, combinations of the foregoing materials, and hydrates of the foregoing materials.

Various materials may be mixed with, associated with, or incorporated into the kaolin to maintain an antiseptic environment at the wound site or to provide functions that are supplemental to the clotting functions of the clay. Exemplary materials that can be used include, but are not limited to, pharmaceutically-active compositions such as antibiotics, antifungal agents, antimicrobial agents, anti-inflammatory agents, analgesics, antihistamines (e.g., cimetidine, chlorpheniramine maleate, diphenhydramine hydrochloride, and promethazine hydrochloride), compounds containing silver or copper ions, combinations of the foregoing, and the like. Other materials that can be incorporated to provide additional hemostatic functions include ascorbic acid, tranexamic acid, rutin, and thrombin. Botanical agents having desirable effects on the wound site may also be added.

For use in the present invention, the kaolin (or other clay material or diatomaceous earth) is preferably in particle form. As used herein, "particles" include beads, pellets, granules, rods, or any other surface morphology or combination of surface morphologies. Irrespective of the surface morphology, the particles are about 0.2 mm (millimeters) to about 10 mm, preferably about 0.5 mm to about 5 mm, and more preferably about 1 mm to about 2 mm in effective diameter. The present invention is not limited in this regard, however, and other particle sizes (e.g., less than about 0.2 mm) are also within the scope of the present invention. The particle size of the kaolin (or other clay material or diatomaceous earth) may be so small so as to be considered powder. If the particle size is considered to be powder, the powder may be impalpable (i.e., tactilely undetectable).

The clay particles can be produced by any of several various methods. Such methods include mixing, extrusion, spheronizing, and the like. Equipment that can be utilized for the mixing, extruding, or spheronizing of the clay is available from Caleva Process Solutions Ltd. in Dorset, United Kingdom. Other methods include the use of a fluid bed or a pelletizing apparatus. Fluid beds for the production of clay particles are available from Glatt Air Technologies in Ramsey, N.J. Disk pelletizers for the production of clay particles are available from Feeco International, Inc., in Green Bay, Wis. Preferably, the clay is extruded through a suitable pelletizing device. The present invention is not limited in this regard, however, as other devices and methods for producing particlized clay are within the scope of the present invention.

The EPK used in the present invention is particlized, dried, and fired to about 600 degrees C. In order to achieve a suitably homogenous mixture of the EPK to form the particles, a relatively high shear is applied to a mass of the EPK using a suitable mixing apparatus. Prior to shearing, the water content of the clay is measured and adjusted to be about 20% by weight to give a sufficiently workable mixture for extrusion and subsequent handling.

During the firing of the EPK to about 600 degrees C., the material is vitrified. Vitrification is effected via repeated melting and cooling cycles to allow the EPK (or other clay material) to be converted into a glassy substance. With increasing numbers of cycles, the crystalline structure is broken down to result in an amorphous composition. The amorphous nature of the EPK allows it to maintain its structural integrity when subsequently wetted. As a result, the EPK maintains its structural integrity when wetted during use, for example, when applied to blood. The present invention is not limited to the use of vitrified clays, however, as clay material that has not been vitrified is still within the scope of the present invention. In particular, unvitrified clay can still be applied to a bleeding wound to provide hemostasis.

It is believed that the cellular clotting mechanism of clay activates certain contact factors when applied to blood. More specifically, it is believed that kaolin (particularly EPK) initiates mechanisms by which water in blood is absorbed to facilitate clotting functions.

Referring now to FIG. 1, one embodiment of a hemostatic device into which the kaolin in particle form is incorporated is shown. The device is a permeable pouch that allows liquid to enter to contact the kaolin particles retained therein. Sealed packaging (not shown) provides a sterile environment for storing the hemostatic device until it can be used. The device, which is shown generally at 10 and is hereinafter referred to as "pouch 10," comprises a screen or mesh 12 and the particlized kaolin 14 retained therein by the screen or mesh. The mesh 12 is closed on all sides and defines openings that are capable of retaining the particlized kaolin 14 therein while allowing liquid to flow through. As illustrated, the mesh 12 is shown as being flattened out, and, by way of example, only a few particles of particlized kaolin 14 are shown. The particlized kaolin 14 may be blended with particles of other types of clay, diatomaceous earth, and the like to form a homogenous mixture.

The mesh 12 is defined by interconnected strands, filaments, or strips of material. The strands, filaments, or strips can be interconnected in any one or a combination of manners including, but not limited to, being woven into a gauze, intertwined, integrally-formed, and the like. Preferably, the interconnection is such that the mesh can flex while substantially maintaining the dimensions of the openings defined thereby. The material from which the strands, filaments or strips are fabricated may be a polymer (e.g., nylon, polyethylene, polypropylene, polyester, or the like), metal, fiberglass, or an organic substance (e.g., cotton, wool, silk, or the like).

Figure 2:
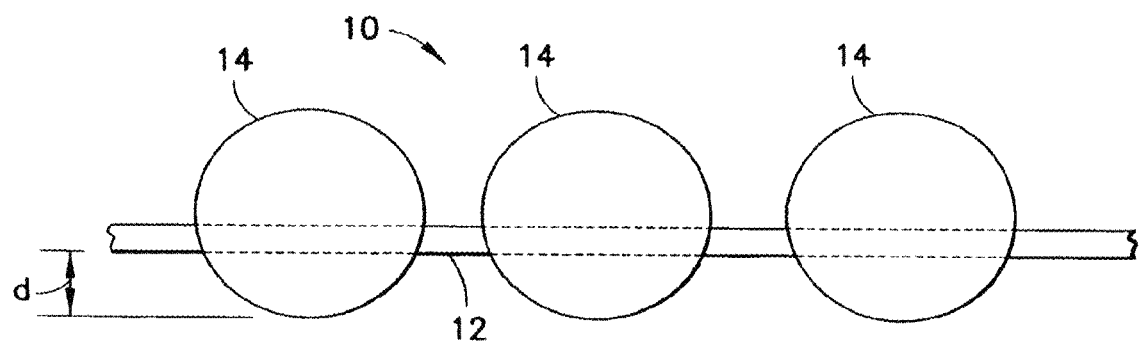
FIG. 2 is a side view of the blood clotting device of FIG. 1 illustrating the retaining of clay particles in the mesh structure.

Referring now to FIG. 2, the openings defined by the mesh 12 are sized to retain the particlized kaolin 14 but permit the flow of blood therethrough. Because the mesh 12 may be pulled tight around the particlized kaolin 14, the particles may extend through the openings by a distance d. If the particles extend through the openings, they will directly contact tissue against which the pouch 10 is applied. Thus, blood emanating from the tissue immediately contacts the particlized kaolin 14, and the water phase thereof is wicked into the kaolin, thereby facilitating the clotting of the blood. However, it is not a requirement of the present invention that the particles protrude through the mesh.

To apply the pouch 10 to a bleeding wound, the pouch is removed from the packaging and placed on the bleeding wound. The particlized kaolin 14 in the mesh 12 contacts the tissue of the wound and/or the blood emanating from the wound, and at least a portion of the liquid phase of the blood is absorbed by the clay material, thereby promoting clotting. The flexibility of the mesh 12 allows the mesh to conform to the shape of the bleeding wound and to retain that shape upon application.

Figure 3:
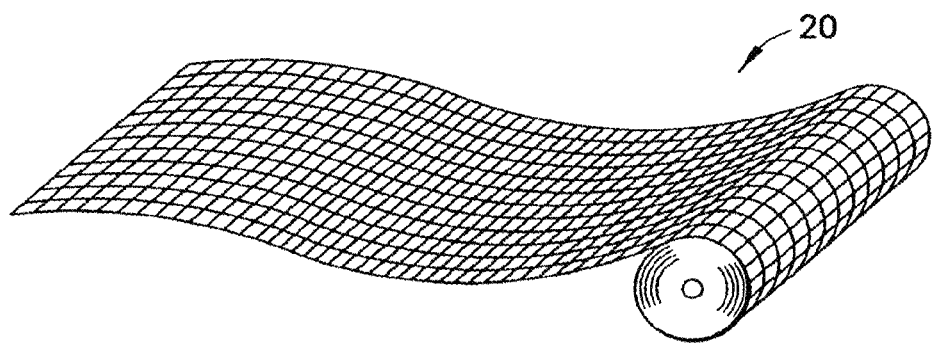
FIG. 3 is a perspective view of a blood clotting device that incorporates a clay material into a gauze.

Referring now to FIG. 3, another embodiment of a hemostatic device of the present invention is a kaolin gauze, which is shown generally at 20 and is hereinafter referred to as "gauze 20." Kaolin is coated onto a gauze substrate using any suitable method to result in the gauze 20. One exemplary method of coating kaolin onto the gauze substrate is to immerse the substrate in a kaolin/water slurry. The kaolin material used for the slurry is preferably finely ground kaolin powder, although the present invention is not limited in this regard as kaolin particles, flakes, chips, beads, rods, granules, or the like may alternatively or additionally be used. The gauze substrate may be any suitable woven or non-woven fibrous material including, but not limited to, cotton, silk, wool, plastic, cellulose, rayon, polyester, combinations of the foregoing, and the like. The present invention is not limited to woven or non-woven fibrous materials as the gauze substrates, however, as felts and the like are also within the scope of the present invention.

The gauze 20 of the present invention is not limited to kaolin, however, as other clays such as attapulgite, bentonite, and combinations thereof may be used in place of or in addition to the kaolin. Furthermore, other silica-based materials such as bioactive glasses, diatomaceous earth, combinations of the foregoing, and the like may also be utilized in addition to or in place of any of the foregoing clay materials.

Once the kaolin is dried onto the gauze substrate to form the gauze 20, the gauze is sufficiently flexible to allow the gauze to be folded, rolled, or otherwise manipulated for packaging.

The flexibility of the substrate of the gauze 20 allows the gauze to form to a shape of the bleeding wound and to retain the shape of the bleeding wound upon application.

One manner of depositing the kaolin (or other clay) coating on the gauze substrate includes heating the kaolin/water slurry. Preferably, the slurry is heated to boiling because higher temperatures tend to facilitate the adhesion of the kaolin to the substrate. The present invention is not limited in this regard, however, as the slurry may be heated to a lower temperature depending on the desired characteristics of the kaolin coating. Boiling the slurry also provides an effective form of agitation that uniformly disperses the kaolin in the liquid phase.

The substrate is then immersed in the boiling slurry for an amount of time sufficient to cause the kaolin to deposit onto the substrate. Given the rheology of wetted kaolin and the material from which the gauze or substrate is fabricated, the kaolin may adhere as a film directly to the surfaces of the substrate, or it may agglomerate in the interstices of the strands as well as along the strands themselves, thereby being trapped in the fiber matrix.

Another manner of depositing the kaolin coating on the substrate includes applying the kaolin in slurry form on one side of the gauze substrate using a spraying technique, a slot die technique, or a combination thereof. In using any technique, the amount of slurry applied to the gauze substrate is limited to avoid or at least minimize the saturation of the substrate. Preferably, a colloidal form of the kaolin (or other clay) is used to provide a stable suspension of the material with suitable viscosity for application using the slot die technique.

Once sprayed or applied using the slot die technique, the coated gauze substrate is then rolled or scraped to further embed the kaolin into the material of the substrate. The gauze substrate is then dried.

In some embodiments, the kaolin may be attached to the gauze substrate using a binder. In embodiments in which a binder is used, the material of the binder is compatible with biological tissue. Preferred binders include polyols, chitosan, and polyvinyl alcohol, all of which have adhesive qualities and are compatible with biological tissue. At least chitosan exhibits hemostatic properties.

One exemplary method for the production of this device may comprise the steps of unwinding gauze from a roll, immersing the gauze in a slurry of hemostatic material and water, applying pressure to the gauze by rolling the wet gauze under high pressure to incorporate the hemostatic material into the material of the gauze, drying the rolled, wet gauze, and removing dust from the gauze (e.g., via blasting with air knives or air nozzles, through the use of electrostatic energy, vacuuming, or brushing with direct contact brushes). Following the removal of dust from the gauze, the gauze back may be wound back onto a roll, or it may be cut into sheets for individual packaging.

One or more variables may be manipulated to optimize the amount and integrity of the kaolin retained on the gauze. These variables include, but are not limited to, slurry temperature, immersion time, the slurry agitation method, and the type of liquid (of the slurry). The elevation of the slurry temperature, as indicated above, aids in the retention of the kaolin on the gauze. The agitation may be effected by forcing air or other gas through nozzles, stirring, bubbling, boiling, or ultrasonic vibration.

The liquid used for the slurry may also be something other than water. For example, the liquid may be an aqueous ammonia solution. Aqueous ammonia has been found to induce swelling in certain fibrous materials, such as the materials typically utilized to fabricate gauze.

In embodiments in which a polyol is used in the gauze 20, the polyol may be glycerol (also known as glycerin, glycerine, glyceritol, glycyl alcohol, and by its chemical name propane-1,2,3-triol). Glycerol is a lubricious, hygroscopic, water-soluble liquid that is compatible with biological tissue. The kaolin is dispersed in the glycerol to form a dispersion or otherwise mixed with the glycerol and is deposited onto the gauze substrate using any suitable method. Suitable methods for depositing the kaolin/glycerol dispersion onto the gauze substrate include, but are not limited to, spraying the dispersion, soaking the gauze substrate in the dispersion, application via slot die techniques, physical means such as brushing or rolling the dispersion onto the gauze, and the like.

The present invention is not limited to the use of glycerol, however, as other glycerol-based compounds including glycerol alcohols (e.g. propylene glycols), glycerol-based esterified fatty acids (e.g., glyceryl triacetates), and other materials having humectant properties and the like (as well as combinations of the foregoing) are within the scope of the present invention. Furthermore, other polyols such as sorbitol, xylitol, maltol, combinations of the foregoing, and the like as well as polymeric polyols (e.g., polydextrose) are also within the scope of the present invention.

Figure 4:
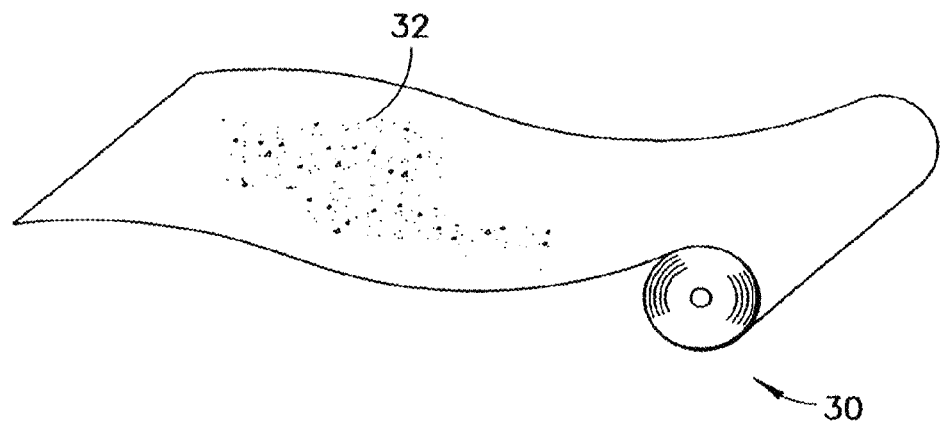
FIG. 4 is a perspective view of a blood clotting device that incorporates a clay material into a cloth.

Referring now to FIG. 4, another embodiment of a hemostatic device of the present invention is a cloth having hemostatic properties, shown generally at 20, and which is hereinafter referred to as "cloth 30." The cloth 30 is a fabric which may be defined by woven or unwoven strands or a felt or the like into which a biological hemostatic material is infused or impregnated. Hemostatic materials that may be infused or impregnated into the fabric of cloth 30 include, but are not limited to, clays (such as kaolin) in the form of particles 32, other silica-based material (such as diatomaceous earth, combinations thereof, or the like), chitosan, combinations of the foregoing, and the like. In embodiments in which such materials are infused or impregnated into a cloth, the material is preferably incorporated into the cloth in a hydrated state and subsequently dried.

In either gauze or cloth embodiments, the gauze or cloth material may be cross-linked with a polysaccharide or similar material.

Figure 5A:
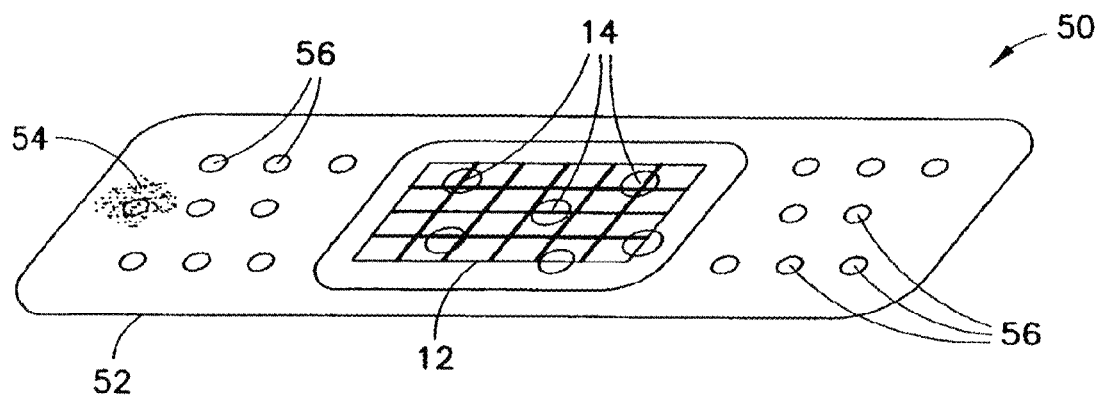
FIG. 5A is a perspective view of a bandage incorporating the clay particles in a mesh container for application to a bleeding wound.

Referring now to FIG. 5A, another embodiment of the present invention is a bandage, shown at 50, which comprises particlized kaolin 14 (or some other clay material or diatomaceous earth) retained in the mesh 12 and mounted to a flexible substrate 52 that can be applied to a wound (for example, using a pressure-sensitive adhesive to adhere the bandage 50 to the skin of a wearer). The mesh 12 is stitched, glued, or otherwise mounted to a substrate 52 to form the bandage 50.

The substrate 52 is a plastic or a cloth member that is conducive to being retained on the skin of an injured person or animal on or proximate a bleeding wound. An adhesive 54 is disposed on a surface of the substrate 52 that engages the skin of the injured person or animal. Particularly if the substrate 52 is a non-breathable plastic material, the substrate may include holes 56 to allow for the dissipation of moisture evaporating from the skin surface.

Figure 5B:
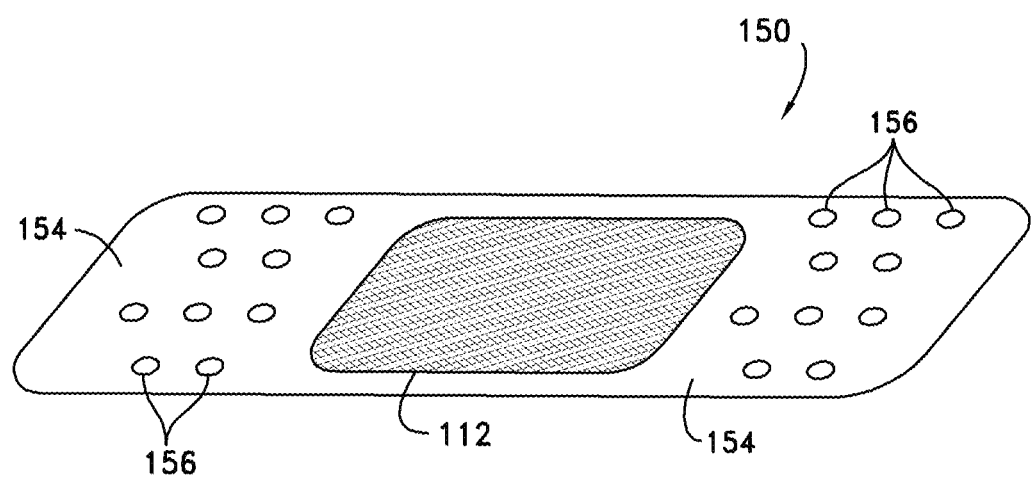
FIG. 5B is a perspective view of a bandage incorporating the hemostatic material and a polyol into a gauze substrate for application to a bleeding wound.

Referring now to FIG. 5B, another embodiment of the bandage is shown at 150. The bandage 150 comprises particlized kaolin (or some other clay material or diatomaceous earth capable of imparting a hemostatic function) dispersed in glycerol and applied to a gauze substrate 112. The gauze substrate 112 is mounted to a flexible substrate 152 that can be applied to a wound (for example, using a pressure-sensitive adhesive 154 disposed over substantially all of a skin-contacting surface of the flexible substrate 152 to adhere the bandage 150 to the skin of a wearer). The gauze substrate 112 is stitched, glued, or otherwise mounted to the substrate 152, which may be a plastic or cloth member that may include holes 156. A release agent (e.g., polyvinyl alcohol, glycerol, carboxymethyl cellulose, or the like) may be disposed over the kaolin/glycerol dispersion on the gauze substrate 112.

Figure 6:
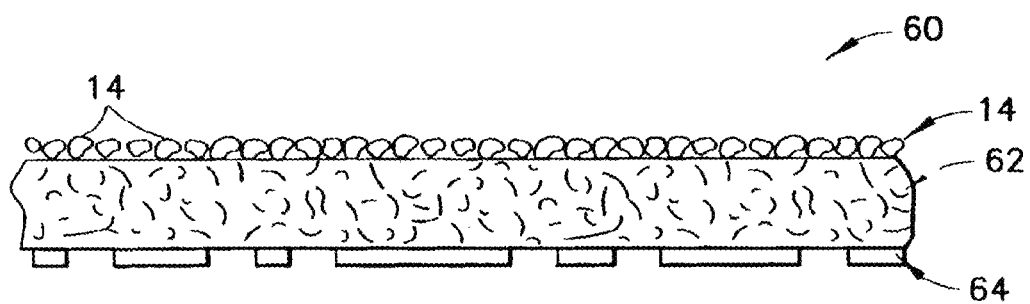
FIG. 6 is a schematic representation of a sponge having hemostatic capabilities.

Referring now to FIG. 6, another embodiment of the present invention is a sponge, shown at 60, which comprises a substrate 62, the particlized kaolin 14 (or some other clay material or diatomaceous earth) disposed on one face of the substrate 62, and a release agent 64 disposed on an opposing face of the substrate. The sponge 60 allows for sufficient contact of the particlized kaolin 14 with blood emanating from a wound and through the release agent 64 and the substrate 62 while minimizing the adhesion of the sponge to the wound tissue. The sponge 60 is also compatible with living tissue.

The substrate 62 is an absorbent gauze material that defines a matrix. The present invention is not so limited, however, as other materials such as rayon/polyester cellulose blends and the like are also within the scope of the present invention. Other materials from which the substrate 62 may be fabricated include woven fabric, non-woven fabric, paper (e.g., kraft paper and the like), and cellulose material (e.g., cotton in the forms of balls, swabs, and the like). Any material from which the substrate 62 may be fabricated may have an elastic quality. When elastic materials are used as the substrate 62, the sponge 60 becomes both a hemostatic device and a pressure bandage, particularly in embodiments in which a surface cohesive agent or mechanical fastener is added to secure the sponge in place over a wound.

The hemostatic agent used in the sponge 60 is not limited to particlized kaolin 14. Other materials such as attapulgite, bentonite, combinations of the foregoing, or a combination of the foregoing with kaolin may be used. The present invention is also not limited to clays, as other materials such as bioactive glass, biological hemostats, diatomaceous earth, combinations thereof, the combinations thereof with clay are also within the scope of the present invention.

The particlized kaolin 14 may be bound to the substrate 62 via coulombic forces, by impregnating or otherwise incorporating the clay or other hemostatic material directly into the material of the substrate, by using a binder, by trapping the hemostatic material within the matrix, or the like.

When using a binder to bind the particlized kaolin 14 to the substrate 62, the binder material may provide additional functionality to the sponge 60. Materials from which the binder may be fabricated include, but are not limited to, chitosan, polyvinyl alcohol, guar gum, gelatinized starches, polysaccharides, cellulose, calcium alginate, and the like, as well as combinations of the foregoing.

In embodiments in which the particlized kaolin 14 is incorporated into the substrate 62 directly, the particlized kaolin may be added during the substrate fabrication. If the substrate is a non-woven gauze material containing rayon and polyester, then the particlized kaolin 14 may be incorporated into or onto the fibers of rayon and polyester. For example, the particlized kaolin 14 may be in powder form and applied to molten polyester, and polyester fibers may be drawn from the polyester/hemostatic material melt. If the substrate is a woven gauze (e.g., cotton), the kaolin 14 in powder form may be incorporated into the cotton threads during formation of the threads.

The particlized kaolin 14 may also be dispersed in glycerol and applied to the substrate 62 via a spray technique, a slot die technique, soaking, brushing, rolling, or the like.

The release agent 64 is a material that is disposed on the wound-contacting side of the substrate 62 to facilitate the easy removal of the sponge 60 from the wound tissue after the formation of blood clots. The release agent 64 may be a continuous film, or it may be discontinuous on the surface of the substrate. One material that may be used as a release agent is polyvinyl alcohol, which is a biocompatible material that may be formed as a thin film and that does not significantly affect the absorbency and liquid permeability of the sponge 60. Another material that may be used as the release agent 64 is glycerol, which may be applied in addition to particlized kaolin 14 dispersed in glycerol. When applied as the release agent 64, the glycerol forms a film over the dispersion of the particlized kaolin 14 in glycerol. Other materials that may be utilized as release agents include, but are not limited to, carboxymethyl cellulose. In any configuration of the sponge 60, the release agent 64 may be applied directly to the wound-contacting surface of the substrate 62.

In the alternative, the release agent 64 may be applied to the non-wound contacting surface of the substrate 62 as a slurry of clay and release agent. In such an embodiment, the concentration of the polyvinyl alcohol or glycerol is such that at least some of the alcohol component thereof seeps to the wound-contacting surface of the substrate 62, while the clay material remains on or near the non-wound contacting surface. In any embodiment, the polyvinyl alcohol or the glycerol serves not only as a release agent, but as an agent that suppresses the dust of the particlized kaolin 14.

Other materials that may be used as release agents that are within the scope of the present invention include, but are not limited to, silicone and gelatinized starches. As with polyvinyl alcohol and glycerol, either may be applied in film form.

The sponge 60 may further include a component that imparts a radiopaque characteristic to the sponge. In such an embodiment, barium sulfate may be incorporated into a slurry that includes the particlized kaolin 14 and applied to the substrate 62.

The sponge 60 may further include water or alcohol, thereby allowing the sponge to be used as a wipe.

Figure 7:
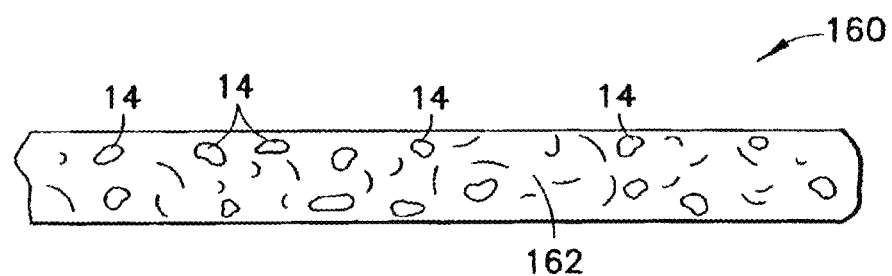
FIG. 7 is a schematic representation of another embodiment of a sponge having hemostatic capabilities.

Referring now to FIG. 7, another embodiment of a sponge is shown generally at 160. The sponge 160 comprises a film 162 into which particlized kaolin 14 is dispersed. The physical integrity of the sponge 160 is maintained by the film 162. Preferably, the material from which the film 162 is fabricated is polyvinyl alcohol. In fabricating the sponge 160, the particlized kaolin 14 is dispersed into polyvinyl alcohol, which is then formed into a sheet. The sponge 160 is especially useful when incorporated into a bandage.

Figure 8:
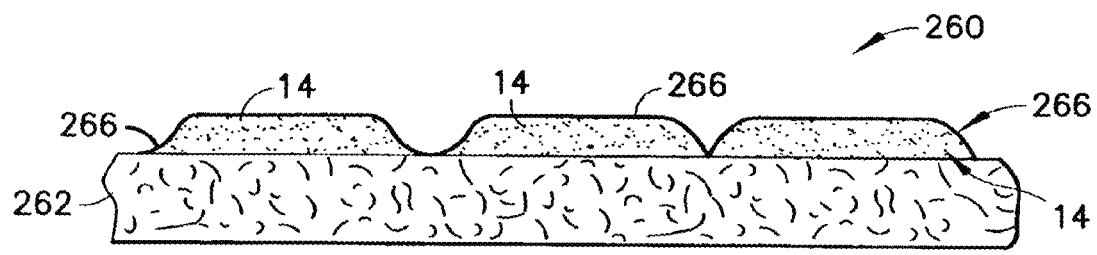
FIG. 8 is a schematic representation of another embodiment of a sponge having hemostatic capabilities.

Referring now to FIG. 8, another embodiment of a sponge is shown generally at 260. The sponge 260 comprises a substrate 262, particlized kaolin 14 disposed on the substrate, and a film 266 disposed over the hemostatic material. The particlized kaolin 14 is unbound (without a binder) blood coagulating agent and is preferably disposed on the substrate 262 in strips to facilitate the folding of the sponge 260. The film 266 is polyvinyl alcohol, glycerol, or the like and is applied to both contain the particlized kaolin 14 and to minimize the generation of dust. Upon application to a bleeding wound, blood from the wound is wicked into the substrate 262 and contacts the particlized kaolin 14.

Figure 9:
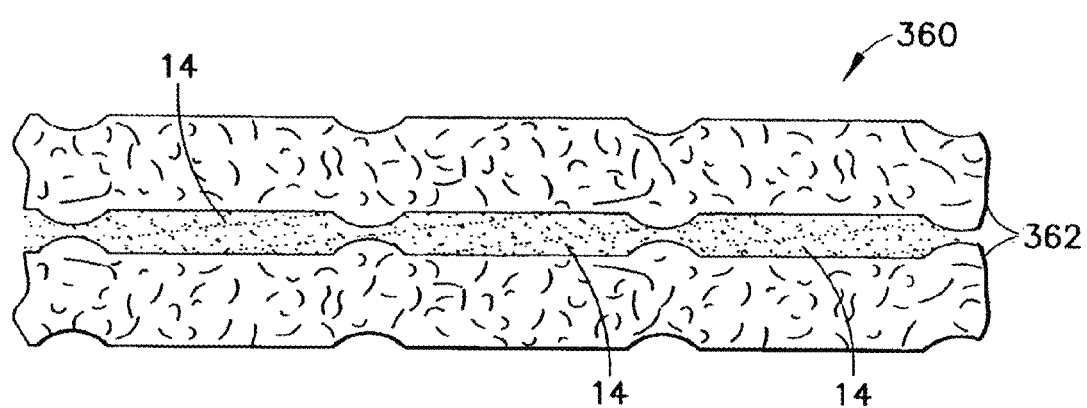
FIG. 9 is a schematic representation of another embodiment of a sponge having hemostatic capabilities.

Referring now to FIG. 9, another embodiment of a sponge is shown generally at 360. The sponge 360 comprises particlized kaolin 14 sandwiched between two substrates 362. The substrates 362 can be bound together in any suitable manner such as heat sealing through areas selectively absent of particlized kaolin 14, using an adhesive or binder in select areas, applying a containment film of material (such as polyvinyl alcohol) over the entire sponge 360, or a combination of any of the foregoing. The particlized kaolin 14 can also be used in conjunction with glycerol, e.g., by being dispersed in glycerol and applied to the sponge 360.

The sponge 60 (as well as the sponges shown at 160, 260, and 360) may be folded and used in various manners. The sponge 60 may be folded such that the surfaces on which the particlized kaolin 14 is disposed are on the inside surfaces of the folded sponge, so as to minimize problems of dusting and detachment of the hemostatic material from the substrate 62. The sponge 60 (and the sponges 160, 260, and 360) can also be folded into a pleated form or into a configuration to produce a number of distinct plies attached along the edges. By configuring the sponge 60 in such a manner, the compliancy and absorbency requirements of different applications can be addressed. The sponge 60 can also be cut or formed into elongated strips for wrapping over the wounds of an injured person or animal or for incorporation into cylinders or swabs. The sponge 60 can also be cut, ripped, ground, or otherwise formed into small pieces for applications such as stuffing into mesh containers.

Example 1—the Effect of Slurry Temperature on the Ability of Cotton Gauze to Retain Kaolin Clay Temperatures of kaolin/water slurries were varied to assess the ability of cotton gauze to retain kaolin clay. Slurries of water and EPK were prepared in which the kaolin was 40% of the total weight of the slurry. Three sponges were made (one from each piece of gauze) by immersing the cotton gauzes into the slurries of varying temperatures, rolling the wet sponges under pressure, and drying. The Table below indicates the parameters for each slurry and the results obtained.

| Sample | Slurry Temp. (degrees ° C.) | Agitation method | Starting gauze weight (grams) | Gauze weight after (grams) | % kaolin (wt. %) |
|---|---|---|---|---|---|
| 1 | 22 | Stir 1 minute | 3.139 | 5.59 | 44 |
| 2 | 90 | Stir 1 minute | 3.064 | 5.868 | 48 |
| 3 | 100 | Boil 1 minute | 3.085 | 6.481 | 52 |

The gauze weight after is the weight of the gauze after rolling and drying. It was noted that the elevated slurry temperature increased the amount of retained kaolin. One theory for this is that the cotton fiber structure of the gauze is loosened and swollen by its immersion in the hot liquid.

Example 2—Application of Dry Kaolin to Dry Cotton Gauze to Form Hemostatic Device Dry kaolin was applied to a dry cotton gauze. The gauze was then rolled. The amount of kaolin retain on the gauze was visibly and significantly less than the amount of kaolin retained on the gauze of Sample 3 (Example 1). This sample, however, accelerated the clot time in sheep whole blood by 70% over the unaccelerated clot time of the blood.

Example 3—Reduction of Kaolin Dust Using Glycerol

A slurry of 50 grams (g) of water, 20 g of glycerol, and 15 g of kaolin powder was prepared and used to saturate a gauze sponge (Kendall Curity 2733). The saturated gauze sponge was dried. The sponge was held and tapped with a pencil over a clean glass surface. A visual determination indicated that no readily discernible dust was removed from the sponge as a result of the tapping.

A second sponge was prepared without glycerol and dried. The second sponge was held and tapped with a pencil over a clean glass surface. A visual determination indicated that a substantial amount of kaolin dust was removed from the second sponge as a result of the tapping.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of the appended claims.

The following is claimed:

1. A hemostatic device comprising:
a flexible absorbent substrate comprising cloth, gauze, mesh, or strands;
a hemostatic aluminum silicate material positioned on or in the substrate in a region configured to contact blood from a bleeding wound;
wherein the substrate initially exists separately from the hemostatic material;
wherein the hemostatic device is configured so that the hemostatic material does not substantially detach from the substrate before use;
wherein the device is configured such that when the blood from the bleeding wound contacts the substrate, the blood interacts with at least some of the hemostatic aluminum silicate material on the substrate, which assists in accelerating clotting; and
wherein the hemostatic aluminum silicate is not a zeolite.

2. The hemostatic device of claim 1, wherein the hemostatic aluminum silicate material is a clay material.

3. The hemostatic device of claim 2, wherein the clay material is kaolin.

4. The hemostatic device of claim 1, wherein the hemostatic material is bound to the substrate using a binder selected from the group consisting of chitosan, polyvinyl alcohol, guar gum, gelatinized starches, polysaccharides, cellulose, calcium alginate, and glycerol.

5. The hemostatic device of claim 1, wherein the hemostatic material is bound to the substrate using a glycerol binder.

6. The hemostatic device of claim 1, wherein the hemostatic device is subjected to a drying process during manufacturing.

7. The hemostatic device of claim 1, wherein the hemostatic device further comprises an additional hemostatic aluminum silicate material.

8. The hemostatic device of claim 1, wherein the hemostatic device is provided in a sealed sterilized package prior to use.

9. The hemostatic device of claim 8, wherein the hemostatic device is not saturated with a liquid when in the sterilized package.

10. A hemostatic device comprising:
a flexible absorbent substrate;
a hemostatic material positioned on or in the substrate in a region configured to contact blood from the bleeding wound during use, the hemostatic material comprising an aluminum silicate;
wherein the substrate initially exists separately from the hemostatic material;
wherein the hemostatic material is adhered to the substrate and is configured to substantially remain on or in the substrate before use; and
wherein the device is configured such that when the blood contacts the substrate, it interacts with at least some of the hemostatic material on the substrate, which assists in accelerating clotting and does not produce heat;
wherein the device is subjected to a drying process during manufacturing.

11. The hemostatic device of claim 10, wherein the hemostatic material is made at least in part by heating kaolin or kaolinite and forming a vitrified or glassy material.

12. The hemostatic device of claim 10, wherein the hemostatic material is applied to the substrate as a slurry comprising water and a binder.

13. The hemostatic device of claim 12, wherein the binder is selected from the group consisting of chitosan, polyvinyl alcohol, guar gum, gelatinized starches, polysaccharides, cellulose, and calcium alginate.

14. The hemostatic device of claim 13, wherein the hemostatic material comprises clay.

15. The hemostatic device of claim 13, wherein the hemostatic material comprises kaolin or kaolinite.

16. The hemostatic device of claim 12, wherein the binder is glycerol.

17. The hemostatic device of claim 16, wherein the hemostatic material comprises clay.

18. The hemostatic device of claim 16, wherein the hemostatic material comprises kaolin or kaolinite.

19. The hemostatic device of claim 10, wherein the hemostatic device comprises carboxymethylcellulose.

20. The hemostatic device of claim 19, wherein the hemostatic material comprises clay.

21. The hemostatic device of claim 19, wherein the hemostatic material comprises kaolin or kaolinite.

22. The hemostatic device of claim 10, wherein the hemostatic device further comprises an additional hemostatic aluminum silicate material.

* * * * *

UNITED STATES PATENT AND TRADEMARK OFFICE
CERTIFICATE OF CORRECTION

| | | |
|---|---|---|
| PATENT NO. | : 12,076,448 B2 | |
| APPLICATION NO. | : 17/407026 | |
| DATED | : September 3, 2024 | |
| INVENTOR(S) | : Raymond J. Huey et al. | |

It is certified that error appears in the above-identified patent and that said Letters Patent is hereby corrected as shown below:

On the Title Page

Page 4, Column 2 item (56) (Other Publications), Line 3, delete "Hemorrage" and insert -- Hemorrhage --.

Page 4, Column 2 item (56) (Other Publications), Line 4, delete "Hemorrages" and insert -- Hemorrhages --.

Page 5, Column 1 item (56) (Other Publications), Line 33, delete "Formatin" and insert -- Formation --.

Page 6, Column 1 item (56) (Other Publications), Line 12, delete "Plyurethane" and insert -- Polyurethane --.

Page 6, Column 1 item (56) (Other Publications), Line 27, delete "Injuary," and insert -- Injury, --.

Page 9, Column 1 item (56) (Other Publications), Line 33, delete "Proposede" and insert -- Proposed --.

In the Specification

Column 9, Line 24, delete "glyceritol," and insert -- glycerol, --.

Signed and Sealed this
Nineteenth Day of November, 2024

Katherine Kelly Vidal
*Director of the United States Patent and Trademark Office*